(12) United States Patent
Pesce et al.

(10) Patent No.: US 8,034,003 B2
(45) Date of Patent: Oct. 11, 2011

(54) TISSUE EXTRACTION AND COLLECTION DEVICE

(75) Inventors: Robert S. Pesce, Norwood, MA (US);
Shelby Cook, Foxboro, MA (US);
Kristian DiMatteo, Waltham, MA (US);
Kevin Ranucci, Warwick, RI (US);
Robert Boock, San Diego, CA (US)

(73) Assignee: DePuy Mitek, Inc., Raynham, MA (US)

( * ) Notice: Subject to any disclaimer, the term of this patent is extended or adjusted under 35 U.S.C. 154(b) by 551 days.

(21) Appl. No.: 12/056,637

(22) Filed: Mar. 27, 2008

(65) Prior Publication Data
US 2008/0234715 A1    Sep. 25, 2008

Related U.S. Application Data

(63) Continuation-in-part of application No. 10/661,460, filed on Sep. 11, 2003, now Pat. No. 7,611,473.

(51) Int. Cl.
*A61B 10/00* (2006.01)

(52) U.S. Cl. ........ 600/564; 600/562; 600/565; 600/566; 600/567; 600/568

(58) Field of Classification Search .......... 600/562–572; 606/80, 167, 180
See application file for complete search history.

(56) References Cited

U.S. PATENT DOCUMENTS

| | | |
|---|---|---|
| 1,337,998 A | 4/1920 | Church |
| 3,604,417 A | 9/1971 | Stolzenberg |
| 3,698,561 A | 10/1972 | Babson |
| 3,810,545 A | 5/1974 | Filz et al. |
| 3,814,079 A | 6/1974 | Le Roy, Sr. |
| 3,937,222 A | 2/1976 | Banko |

(Continued)

FOREIGN PATENT DOCUMENTS

EP    0527312    2/1993

(Continued)

OTHER PUBLICATIONS

Albrecht, "The Closure of Joint Cartilage Defects by Means of Cartilage Fragments and Fibrin Adhesive," Fortschr. Med. 101 37:1650-1652 (1983).

(Continued)

*Primary Examiner* — Jeffrey G Hoekstra

(57) ABSTRACT

Methods and device for extracting and collecting tissue, which can be used for example in tissue engineering and grafting applications, are disclosed. In one embodiment, a device can include an outer tube. A rotatable shaft can be disposed within the outer tube can have a tissue harvesting tip formed on its distal end, the tissue harvesting tip being effective to excise tissue upon rotation thereof. A tissue collection device can be included to receive and collected excised tissue, and the tissue collection device can indicate the amount of tissue collected therein. For example, the tissue collection device can include a straining element which collects excised tissue and an indicator by which to assess the amount of collected tissue. In some embodiments, the tissue collection device can translate to indicate the amount of collected tissue. In many cases, devices disclosed herein can include driving mechanisms that are adapted to drive a tissue harvesting tip such that the tip excises soft tissue, but stops when contacting bone (or soon after contacting bone). In some embodiments, the tissue harvesting tip can be effective to excise viable tissue samples, such that the samples can exhibit desirable proportions of viable cells. Further, in some embodiments, the tissue harvesting tips can excise a tissue sample with tissue particles falling in certain size ranges.

27 Claims, 35 Drawing Sheets

U.S. PATENT DOCUMENTS

| | | |
|---|---|---|
| 4,366,822 A | 1/1983 | Altshuler |
| 4,438,769 A | 3/1984 | Pratt et al. |
| 4,469,153 A | 9/1984 | Morrisette |
| 4,553,553 A | 11/1985 | Homann et al. |
| 4,649,919 A | 3/1987 | Thimsen et al. |
| 4,690,672 A | 9/1987 | Veltrup et al. |
| 4,842,578 A | 6/1989 | Johnson et al. |
| 4,844,064 A | 7/1989 | Thimsen et al. |
| 4,960,130 A | 10/1990 | Guirguis |
| 5,041,138 A | 8/1991 | Vacanti et al. |
| 5,077,012 A | 12/1991 | Guirguis |
| 5,108,381 A | 4/1992 | Kolozsi |
| 5,108,422 A | 4/1992 | Green et al. |
| 5,186,714 A | 2/1993 | Boudreault et al. |
| 5,195,956 A | 3/1993 | Stockmeier et al. |
| 5,197,483 A | 3/1993 | Rogalsky et al. |
| 5,206,023 A | 4/1993 | Hunziker et al. |
| 5,252,301 A | 10/1993 | Nilson et al. |
| 5,269,785 A | 12/1993 | Bonutti |
| 5,333,627 A | 8/1994 | Mehringer et al. |
| 5,338,294 A | 8/1994 | Blake, III |
| 5,370,609 A | 12/1994 | Drasler et al. |
| 5,387,236 A | 2/1995 | Noishiki et al. |
| 5,398,690 A | 3/1995 | Batten et al. |
| 5,403,317 A | 4/1995 | Bonutti |
| 5,489,291 A | 2/1996 | Wiley |
| 5,494,044 A | 2/1996 | Sundberg |
| 5,526,822 A | 6/1996 | Burbank et al. |
| 5,527,330 A | 6/1996 | Tovey |
| 5,551,778 A | 9/1996 | Hauke et al. |
| 5,575,293 A * | 11/1996 | Miller et al. ............... 600/565 |
| 5,593,423 A | 1/1997 | Person et al. |
| 5,649,547 A * | 7/1997 | Ritchart et al. ............ 600/566 |
| 5,694,951 A | 12/1997 | Bonutti |
| 5,759,190 A | 6/1998 | Vibe-Hansen et al. |
| 5,788,667 A | 8/1998 | Stoller |
| 5,804,366 A | 9/1998 | Hu et al. |
| 5,827,305 A | 10/1998 | Gordon |
| 5,871,454 A | 2/1999 | Majlessi |
| 5,871,462 A | 2/1999 | Yoder et al. |
| 5,900,361 A | 5/1999 | Klebe |
| 5,913,859 A | 6/1999 | Shapira |
| 5,944,686 A | 8/1999 | Patterson et al. |
| 5,949,044 A | 9/1999 | Walker et al. |
| 6,010,476 A | 1/2000 | Saadat |
| 6,017,348 A | 1/2000 | Hart et al. |
| 6,022,354 A | 2/2000 | Mercuri et al. |
| 6,053,923 A | 4/2000 | Veca et al. |
| 6,066,153 A | 5/2000 | Lev et al. |
| 6,071,284 A | 6/2000 | Fox |
| 6,110,176 A | 8/2000 | Shapira |
| 6,120,514 A | 9/2000 | Vibe-Hansen et al. |
| 6,135,977 A | 10/2000 | Drasler et al. |
| 6,174,313 B1 | 1/2001 | Bonutti |
| 6,179,840 B1 | 1/2001 | Bowman |
| 6,214,369 B1 | 4/2001 | Grande et al. |
| 6,216,573 B1 | 4/2001 | Moutafis et al. |
| 6,218,182 B1 | 4/2001 | Naughton et al. |
| 6,242,247 B1 | 6/2001 | Rieser et al. |
| 6,280,398 B1 | 8/2001 | Ritchart et al. |
| 6,299,763 B1 | 10/2001 | Ashman |
| 6,325,806 B1 | 12/2001 | Fox |
| 6,352,555 B1 | 3/2002 | Dzau et al. |
| 6,358,252 B1 | 3/2002 | Shapira |
| 6,364,884 B1 | 4/2002 | Bowman et al. |
| 6,375,635 B1 | 4/2002 | Moutafis et al. |
| 6,378,527 B1 | 4/2002 | Hungerford et al. |
| 6,402,766 B2 | 6/2002 | Bowman et al. |
| 6,423,073 B2 | 7/2002 | Bowman |
| 6,436,110 B2 | 8/2002 | Bowman et al. |
| 6,447,517 B1 | 9/2002 | Bowman |
| 6,451,017 B1 | 9/2002 | Moutafis et al. |
| 6,485,436 B1 | 11/2002 | Truckai et al. |
| 6,497,707 B1 | 12/2002 | Bowman et al. |
| 6,511,493 B1 | 1/2003 | Moutafis et al. |
| 6,537,567 B1 | 3/2003 | Niklason et al. |
| 6,543,455 B2 | 4/2003 | Bonutti |
| 6,554,852 B1 | 4/2003 | Oberlander |
| 6,572,578 B1 | 6/2003 | Blanchard |
| 6,669,710 B2 | 12/2003 | Moutafis et al. |
| 6,736,799 B1 | 5/2004 | Erbe et al. |
| D491,807 S | 6/2004 | Cauldwell et al. |
| D494,063 S | 8/2004 | Cauldwell et al. |
| 6,783,532 B2 | 8/2004 | Steiner et al. |
| 6,846,314 B2 | 1/2005 | Shapira |
| 6,852,330 B2 | 2/2005 | Bowman et al. |
| 6,875,442 B2 | 4/2005 | Holy et al. |
| 6,878,338 B2 | 4/2005 | Taylor et al. |
| 6,884,428 B2 | 4/2005 | Binette et al. |
| 6,921,380 B1 | 7/2005 | Epstein et al. |
| 7,115,100 B2 | 10/2006 | McRury |
| 7,270,284 B2 | 9/2007 | Liao et al. |
| 7,611,473 B2 | 11/2009 | Boock et al. |
| 7,794,408 B2 | 9/2010 | Binette et al. |
| 2001/0043918 A1 | 11/2001 | Masini et al. |
| 2002/0007190 A1 | 1/2002 | Wulfman et al. |
| 2002/0029055 A1 | 3/2002 | Bonutti |
| 2002/0045903 A1 | 4/2002 | Bonutti |
| 2002/0052628 A1 | 5/2002 | Bowman |
| 2002/0055755 A1 | 5/2002 | Bonutti |
| 2002/0082631 A1 | 6/2002 | Bonutti |
| 2002/0091401 A1 | 7/2002 | Hellenkamp |
| 2002/0091403 A1 | 7/2002 | Bonutti |
| 2002/0091406 A1 | 7/2002 | Bonutti |
| 2002/0095157 A1 | 7/2002 | Bowman |
| 2002/0099401 A1 | 7/2002 | Bonutti |
| 2002/0099403 A1 | 7/2002 | Yoo |
| 2002/0106625 A1 | 8/2002 | Hung et al. |
| 2002/0119177 A1 | 8/2002 | Bowman et al. |
| 2002/0127265 A1 | 9/2002 | Bowman et al. |
| 2002/0161449 A1 | 10/2002 | Muschler |
| 2002/0169465 A1 | 11/2002 | Bowman et al. |
| 2002/0177802 A1 | 11/2002 | Moutafis et al. |
| 2003/0009237 A1 | 1/2003 | Bonutti |
| 2003/0012805 A1 | 1/2003 | Chen et al. |
| 2003/0032961 A1 | 2/2003 | Pelo et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0114875 A1 | 6/2003 | Sjostrom |
| 2003/0114936 A1 | 6/2003 | Sherwood et al. |
| 2003/0147935 A1 | 8/2003 | Binette et al. |
| 2003/0176881 A1 | 9/2003 | Barlev |
| 2003/0212456 A1 | 11/2003 | Lipchitz et al. |
| 2003/0225344 A1 | 12/2003 | Miller |
| 2004/0010320 A1 | 1/2004 | Huckle et al. |
| 2004/0078090 A1 | 4/2004 | Binette et al. |
| 2004/0092992 A1 | 5/2004 | Adams et al. |
| 2004/0097829 A1 | 5/2004 | McRury et al. |
| 2004/0121459 A1 | 6/2004 | Liao et al. |
| 2004/0126405 A1 | 7/2004 | Sahatjian et al. |
| 2004/0134502 A1 | 7/2004 | Mizuno et al. |
| 2004/0138664 A1 | 7/2004 | Bowman |
| 2004/0142861 A1 | 7/2004 | Mansbridge |
| 2004/0146546 A1 | 7/2004 | Gravett et al. |
| 2004/0169311 A1 | 9/2004 | Bonutti |
| 2004/0175408 A1 | 9/2004 | Chun et al. |
| 2004/0193071 A1 | 9/2004 | Binette et al. |
| 2004/0219182 A1 | 11/2004 | Gomes et al. |
| 2004/0243157 A1 | 12/2004 | Connor et al. |
| 2004/0267362 A1 | 12/2004 | Hwang et al. |
| 2005/0014252 A1 | 1/2005 | Chu et al. |
| 2005/0021035 A1 | 1/2005 | Groiso |
| 2005/0038520 A1 | 2/2005 | Binette et al. |
| 2005/0048644 A1 | 3/2005 | Hedrick et al. |
| 2005/0059905 A1 | 3/2005 | Boock et al. |
| 2005/0059986 A1 | 3/2005 | Bowman |
| 2005/0107814 A1 | 5/2005 | Johnston et al. |
| 2005/0113736 A1 | 5/2005 | Orr et al. |
| 2005/0113937 A1 | 5/2005 | Binette et al. |
| 2005/0113938 A1 | 5/2005 | Jamiolkowski et al. |
| 2005/0125077 A1 | 6/2005 | Harmon et al. |
| 2005/0177249 A1 | 8/2005 | Kladakis et al. |
| 2005/0203527 A1 | 9/2005 | Carrison et al. |
| 2005/0222687 A1 | 10/2005 | Vunjak-Novakovic et al. |
| 2005/0232967 A1 | 10/2005 | Kladakis et al. |
| 2005/0234549 A1 | 10/2005 | Kladakis et al. |

| | | | |
|---|---|---|---|
| 2006/0100569 | A1 | 5/2006 | McRury et al. |
| 2006/0129086 | A1 | 6/2006 | McRury et al. |
| 2007/0032740 | A1 | 2/2007 | Quick et al. |
| 2007/0239067 | A1 | 10/2007 | Hibner |
| 2008/0071192 | A1 | 3/2008 | Hynes |
| 2008/0114389 | A1 | 5/2008 | Johnston et al. |
| 2008/0234715 | A1 | 9/2008 | Pesce et al. |
| 2010/0022915 | A1 | 1/2010 | Boock et al. |
| 2010/0280406 | A1 | 11/2010 | Binette et al. |

FOREIGN PATENT DOCUMENTS

| | | |
|---|---|---|
| EP | 1389548 | 2/2004 |
| EP | 1433423 | 6/2004 |
| EP | 1514521 | 3/2008 |
| JP | 3136640 A | 6/1991 |
| JP | 2001505460 T | 4/2001 |
| JP | 2001524844 T | 12/2001 |
| JP | 2003320013 A | 11/2003 |
| JP | 2004121167 A | 4/2004 |
| WO | 9601135 | 1/1996 |
| WO | 9824372 A1 | 6/1998 |
| WO | 9824373 A1 | 6/1998 |
| WO | 9958066 A1 | 11/1999 |
| WO | 9959500 | 11/1999 |
| WO | 0041648 | 7/2000 |
| WO | 0215950 A1 | 2/2002 |
| WO | 02089722 | 11/2002 |
| WO | 03045259 | 6/2003 |
| WO | 2005086874 A2 | 9/2005 |
| WO | 2007112751 | 10/2007 |

OTHER PUBLICATIONS

EP Search Report, Jun. 18, 2009, EP Appln. 09250905.8.
Australian Office Action dated Dec. 16, 2004 for AU Appl. No. 2004201201.
Australian Office Action dated Oct. 17, 2007 for AU Appl. No. 2005242152.
Australian Office Action dated Sep. 4, 2007 for AU Appl. No. 2005229679.
Canadian Office Action dated Feb. 9, 2010 for Canadian Appl. No. 2480704.
Canadian Office Action dated Jul. 17, 2008 for Canadian Appl. No. 2529014.
Canadian Office Action dated Jul. 27, 2010 for Canadian Appl. No. 2462392.
Canadian Office Action dated May 13, 2008 for Canadian Appl. No. 2480704.
Canadian Office Action dated May 21, 2009 for Canadian Appl. No. 2462392.
Canadian Office Action dated Sep. 5, 2007 for Canadian Appl. No. 2529014.
EP Office Action dated Apr. 28, 2010 for EP Appl. No. 09250905.
EP Office Action dated Jun. 25, 2007 for EP Appl. No. 04251843.
EP Office Action dated Nov. 14, 2007 for EP Appl. No. 04255506.
EP Search Report dated Dec. 16, 2004 for EP Appl. No. 04255506.
EP Search Report dated Feb. 22, 2005 for EP Appl. No. 04251843.
EP Search Report dated Jun. 9, 2006 for EP Appl. No. 05257636.
EP Search Report dated Mar. 6, 2006 for EP Appl. No. 05256936.
EP Search Report dated Sep. 16, 2009 for EP Appl. No. 09250905.
Japanese Office Action dated Aug. 24, 2010 for Japanese App. No. 2004-092799.
Japanese Office Action dated Sep. 7, 2010 for Japanese Appl. No. 2004-264265.
Canadian Office Action dated Mar. 12, 2009 for Canadian Application No. 2,480,704 (4 pages).
Canadian Application No. 2480704 dated Mar. 12, 2009, (6 pages).
EP Search Report, Jan. 21, 2011, EP Appln. 10179808.

* cited by examiner

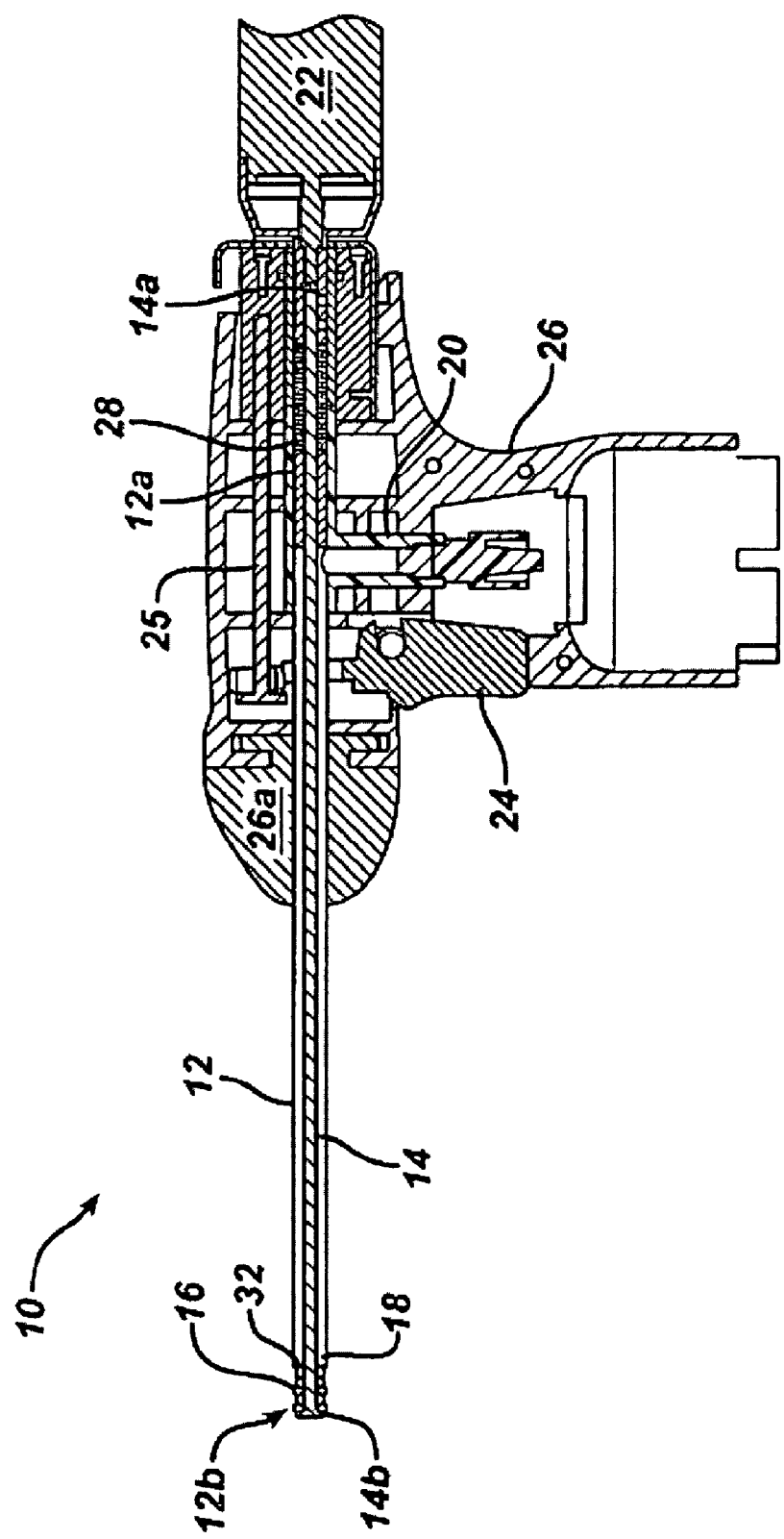

TISSUE EXTRACTION AND COLLECTION DEVICE

The present application is a continuation-in-part of U.S. application Ser. No. 10/661,460, filed on Sep. 11, 2003, and titled "Tissue Extraction and Maceration Device," (now published as U.S. Patent Publication No. 2005/0059905), the teachings of which are hereby incorporated by reference in their entireties.

FIELD

The present application generally relates to methods and devices for extracting and collecting tissue.

BACKGROUND

Tissue grafts are often used to treat gaps, lesions, or other defects in tissue that are caused by trauma, infection or chronic degeneration, joint revision surgery, and oral/maxillofacial surgery. Bone grafts also can be used to treat fractures, gaps, or other defects in bone. Grafts provide a framework into which the host tissue can regenerate and heal. Once implanted, the living cells integrate into the porous microstructure of the graft to support the new tissue as it grows to repair damaged areas.

The loss or failure of tissue is one of the most frequent and costly problems in human health care. In recent years, grafting has evolved from autograft and allograft preparations to biosynthetic and tissue-engineered living replacements. Tissue engineering enables the growth of transplantable functional tissue replacements starting from samples of autologous cells of the patient. The autologous cells are obtained by harvesting tissue from a patient using a biopsy and then cells are extracted from the tissue sample and cultured to the appropriate numbers in the laboratory. These living cells are then placed in a three-dimensional natural or synthetic scaffold or matrix, and are kept under tissue-specific culture conditions to ensure differentiation and tissue maturation. If provided with the appropriate conditions and signals, the cells will secrete various matrix materials to create living tissue that can be implanted back into the defective site in the patient.

Current tissue engineering procedures involve a multi-step process. First, a biopsy is performed to remove a tissue sample from a patient's body. A variety of biopsy devices are well known in the art, including, for example, high-pressure fluid jets that are effective to cut and retrieve a tissue sample. Once the biopsy procedure is complete, the tissue sample is sent to a laboratory, where cells are isolated from the tissue sample. The isolated cells can then be placed into a three-dimensional scaffold for subsequent growth and eventually, implantation back into the patient in a second surgical procedure.

While current procedures have proven effective, they can be very time-consuming, costly, and involve multiple surgical procedures. Accordingly, there exists a need for more efficient and effective methods and devices for obtaining and processing a tissue sample. There also remains a need for an improved tissue extraction device that maximizes cell viability and that provides surgeons with an efficient, easy-to-use device in a compact form.

SUMMARY

In one embodiment, a tissue extraction and collection device is provided which includes an outer tube and a shaft rotatably disposed within the outer tube. The shaft can have a tissue harvesting tip disposed at its distal end, and the tissue harvesting tip can be effective to excise tissue upon rotation. In addition, the device can have a tissue collection device coupled to the outer tube for receiving excised tissue and fluid flow therefrom. In some embodiments, the tissue collection device can be configured to indicate an amount of excised tissue collected via one or more indicators. In other embodiments, the tissue collection device can be configured to indicate the amount of collected excised tissue via one or more indicators that indicates displacement of a portion of the tissue collection device.

A wide range of variations are possible. In some embodiments, for example, the tissue extraction and collection device can further include a handle housing from which the outer tube extends. In other embodiments, a drive mechanism, such as an electric motor, or a motor and/or gearing mechanism, can be coupled to the shaft and effective to rotate the shaft, for example, at a speed in the range of about 100 to 5000 rpm. The driver mechanism can be battery powered. In certain exemplary embodiments, the tissue extraction and collection device can include a vacuum source that is coupled to the tissue collection device and that is effective to draw tissue through at least a portion of the tissue collection device.

The tissue collection device can have a variety of configurations. In one embodiment, the tissue collection device can include a container having an inlet and an outlet for receiving fluid flow therethrough, and a tissue collection chamber disposed in the container for receiving fluid flow through the container. The tissue collection chamber can include a straining element, such as a mesh, filter, screen, or perforated surface, for collecting tissue and passing fluid. In some embodiments, the tissue collection chamber can be movably disposed. For example, the tissue collection chamber can be translatable along a longitudinal axis thereof such that fluid flow through the container is effective to translate the tissue collection chamber within the container. A biasing element, such as a spring or an elastomeric element, can be included to bias the tissue collection chamber along the longitudinal axis. In such an embodiment, fluid flow through the container can be effective to overcome the biasing element to translate the tissue collection chamber within the container such that the displacement of the tissue collection chamber corresponds to an amount of tissue in the tissue collection chamber. In some embodiments, at least a portion of the tissue collection chamber can extend across a lumen formed in the container such that substantially all fluid flow through the container flows through the tissue collection chamber.

The tissue collection device can also include one or more visual indicators, such as a reference line, disposed on a substantially transparent portion of the container or on the tissue collection chamber to indicate the amount of collected tissue in the tissue collection device. In some embodiments, the one or more visual indicators can indicate a degree of displacement of the tissue collection chamber which corresponds to the amount of tissue in the tissue collection chamber. In some cases, the visual indicator on the tissue collection chamber can be referenced or matched to the visual indicator on the container. In yet further embodiments, the tissue collection device can include one or more visual indicators disposed on the tissue collection chamber to indicate a degree of displacement of the tissue collection chamber, which can correspond to the amount of tissue in the tissue collection chamber. For example, the visual indicator can be adapted to indicate when about 50-1000 mg of tissue is disposed in the tissue collection device or tissue collection chamber.

In another embodiment, an exemplary tissue extraction device can include a tissue harvesting tip rotatably disposed at the distal end of a shaft. The tissue harvesting tip can be effective to excise tissue upon rotation thereof. The tissue harvesting tip can also have a lumen for receiving excised tissue therein. A driver mechanism can be coupled to the tissue harvesting tip and can apply a torque to the tissue harvesting tip such that the tissue harvesting tip rotates to excise soft tissue, such as cartilage (including cartilage from a patient's knee), and stops rotating when the tissue harvesting tip contacts bone. The tissue harvesting tip can stop sufficiently fast so as to produce a tissue sample substantially free of bone contamination. In some embodiments, such a tissue sample can have less than about 10% bone contamination, and in other embodiments, it can have less than about 5% bone contamination (more preferably about 1%). In some embodiments, the applied torque can be a range of about 1 to 5 N-cm, or in other embodiments in a range of about 2 to 3 N-cm. The driver mechanism can include a motor and one or more gears configured to provide the applied torque. The driver mechanism can be effective to rotate the tissue harvesting tip at a speed of about 100 rpm to 5000 rpm, or in some embodiments at a speed of about 2000 rpm to 3000 rpm. The tissue extraction device can have a variety of other features as well. For example, the tissue extraction device can include a vacuum source coupled to the tissue harvesting tip for evacuating excised tissue therethrough. The tissue extraction device can also include a tissue collection device coupled to the tissue harvesting tip for receiving excised tissue therefrom, the tissue collection device including a tissue scaffold.

In yet another embodiment, an exemplary tissue extraction device can include a tissue harvesting tip rotatably disposed at a distal end of a shaft, and a driver mechanism coupled to the tissue harvesting tip and effective to rotate the tissue harvesting tip. The tissue extraction device can include a tissue collection device coupled to the tissue harvesting tip for receiving excised tissue therefrom, the tissue collection device including a tissue scaffold. The tissue harvesting tip can have a wide variety of features. For example, the tissue harvesting tip can be effective to excise a viable tissue sample, (such as a soft tissue sample, cartilage tissue sample, and/or a tissue example substantially free of bone material) upon rotation thereof. For example, in some embodiments, at least about 50 percent, more preferably greater than 70 percent of cells in the tissue sample represents living cells capable of migration from the tissue sample. Further, the tissue harvesting tip can include a substantially cylindrical or conical tip with one or more openings formed therein for allowing excised tissue to pass therethrough. The tissue harvesting tip can include cutting surfaces disposed at least partially around the one or more openings and configured to cut tissue upon its rotation.

In yet another embodiment, an exemplary tissue extraction device can include a tissue harvesting tip rotatably disposed at the distal end of a shaft and a driver mechanism coupled to the tissue harvesting tip and effective to rotate the tissue harvesting tip. The tissue extraction device can also include a tissue collection device coupled to the tissue harvesting tip for receiving excised tissue therefrom, the tissue collection device including a tissue scaffold. The tissue harvesting tip can have a wide variety of features. For example, the tissue harvesting tip can be effective to excise tissue particles (such as soft tissue particles, and/or cartilage tissue particles, or others) upon rotation thereof, at least some of the excised tissue particles are tissue particles that each having a size in a range of about 0.01 $mm^3$ to 3 $mm^3$. For example in some embodiments, at least about 90 percent of the excised tissue particles are tissue particles that each have a size in a range of about 0.01 $mm^3$ to 3 $mm^3$, and in other embodiments, at least about 50 percent of the excised tissue particles are tissue particles that each have a size in a range of about 0.01 $mm^3$ to 1 $mm^3$. The tissue harvesting tip can have cutting surfaces disposed at least partially around one or more openings and can be configured to cut tissue upon its rotation. In some embodiments, the one or more openings can be about 2 mm across.

In other aspects, methods for extracting and collecting tissue are provided. A variety of techniques can be used. However, in one embodiment, an exemplary method can include excising tissue with a rotatable tissue harvesting tip formed at a distal end of a rotatable shaft, and transporting the excised tissue to a tissue collection device via the vacuum force. The method can also include indicating an amount of excised tissue collected in the tissue collection device via one or more indicators on the tissue collection device. To indicate the amount of excised tissue, for example, the amount of collected tissue can be compared to an indicator, or the displacement of a portion of the tissue collection device can be indicated. For example, a tissue collection chamber within a container in the tissue collection device can be moved (for example, translated) such that displacement of the tissue collection chamber corresponds to an amount of tissue in the tissue collection chamber. In some embodiments, one or more visual indicators can be disposed on a substantially transparent portion of the tissue collection device, and the one or more visual indicators can indicate a degree of displacement of the tissue collection chamber which corresponds to the amount of tissue in the tissue collection chamber. The method can also include removing excised tissue from the tissue collection device, which can be accomplished for example by directing a flow of fluid through the tissue collection device, and depositing excised tissue onto a tissue scaffold.

BRIEF DESCRIPTION OF THE DRAWINGS

The invention will be more fully understood from the following detailed description taken in conjunction with the accompanying drawings, in which:

FIG. 1B is a cross-sectional view of the tissue extraction and maceration device shown in FIG. 1A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present application.

The present application generally provides methods and devices useful for extracting and/or collecting tissue. The present application provides devices and methods for extracting and macerating tissue, and optionally for depositing the tissue onto a tissue scaffold. The methods and devices can be used to extract a viable tissue sample of appropriate volume and containing tissue particles of an appropriate shape and/or size for incorporation onto a tissue scaffold or in other tissue engineering techniques. For example, in some cases the methods and devices can be used to harvest and process cartilage harvested or other tissue from a body, in many cases in a fluid environment. Further, in some cases the method and devices can be used to harvest and process cartilage without harvesting undesirable amounts of underlying bone (or other underlying tissue). However, the foregoing is by way of example only and it should be understood that the methods and devices described herein have wide applicability, including biopsy and tissue harvesting for a range of purposes and procedures.

Figure 1A:
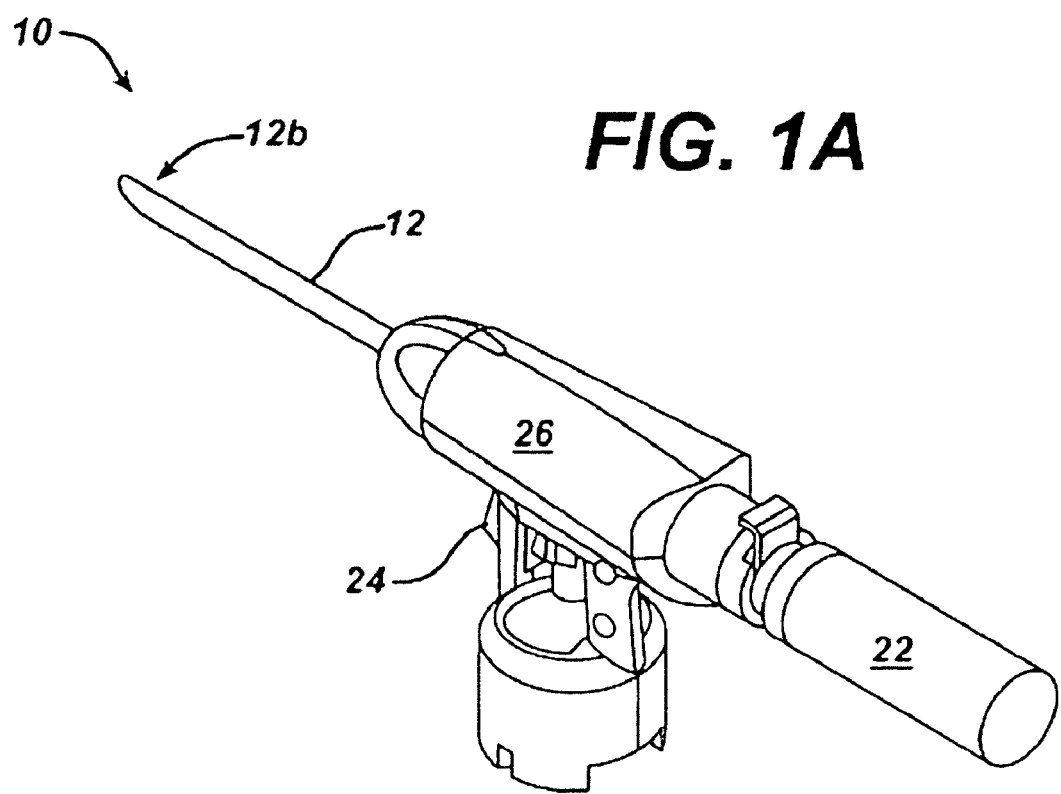
FIG. 1A is a perspective view of a tissue extraction and maceration device according to one embodiment of the present invention.

As shown in FIGS. 1A-1B, the device 10 generally includes an outer tube 12 having a substantially open distal end 12b that is adapted to be placed on and preferably to form a seal with a tissue surface, and a shaft 14 (FIG. 1B) rotatably disposed within the outer tube 12. The shaft 14 is movable between a first, proximal position, as shown in FIG. 1B, in which the shaft 14 is fully disposed within the outer tube 12, and a second, distal position (not shown) in which a portion of a distal end 14b of the shaft 14 extends through the opening in the distal end 12b of the outer tube 12. The device 10 also includes a tissue harvesting tip 16 formed on the distal end 14b of the shaft 14 that is effective to excise a tissue sample when the shaft 14 is moved to the distal position, and a cutting member 18 that is coupled to the shaft 14 at a position proximal to the tissue harvesting tip 16. The cutting member 18 is effective to macerate a tissue sample excised by the tissue harvesting tip 16. In an exemplary embodiment, the components of the device 10 are positioned within an outer housing 26 that extends around a portion of the outer tube 12 and that has a shape that facilitates handling of the device 10.

The device can be particularly advantageous in that it can provide a simple, all-in-one device that can be operated using one hand. The device is designed to effectively remove a viable tissue sample, to control the volume of tissue removed, and to macerate the tissue sample into particles having a predetermined size.

Figure 2A:
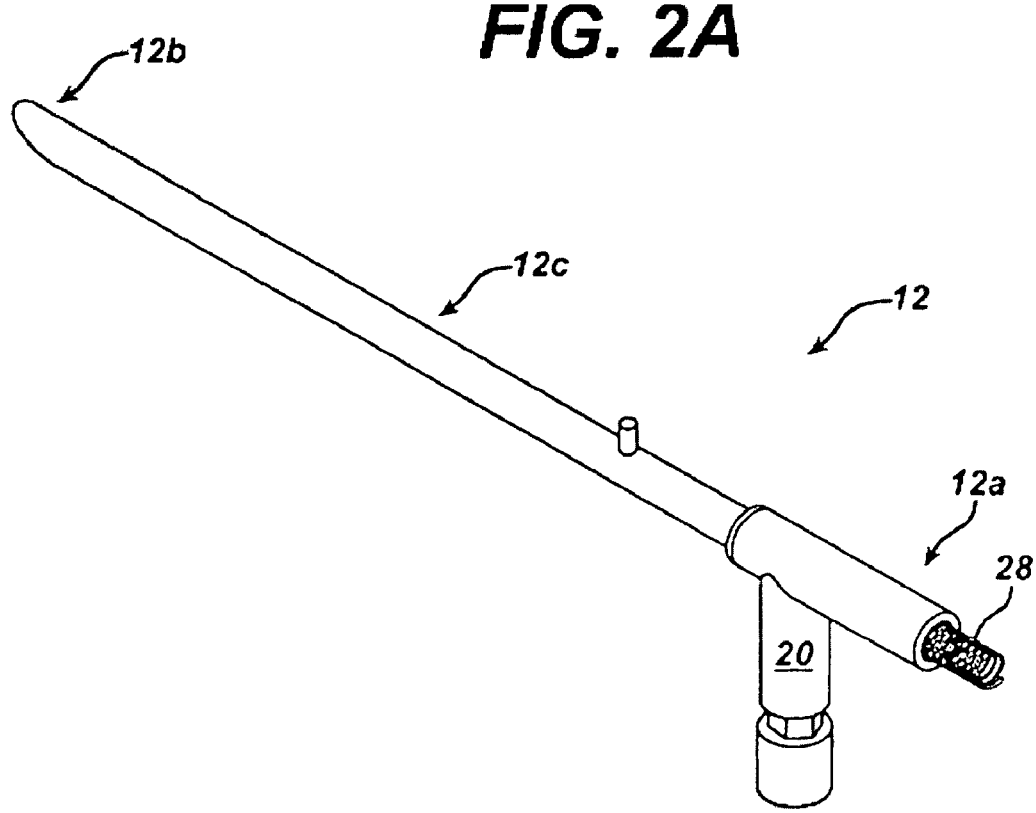
FIG. 2A is a perspective view of the outer tube of the tissue extraction and maceration device shown in FIGS. 1A and 1B.
Figure 2B:
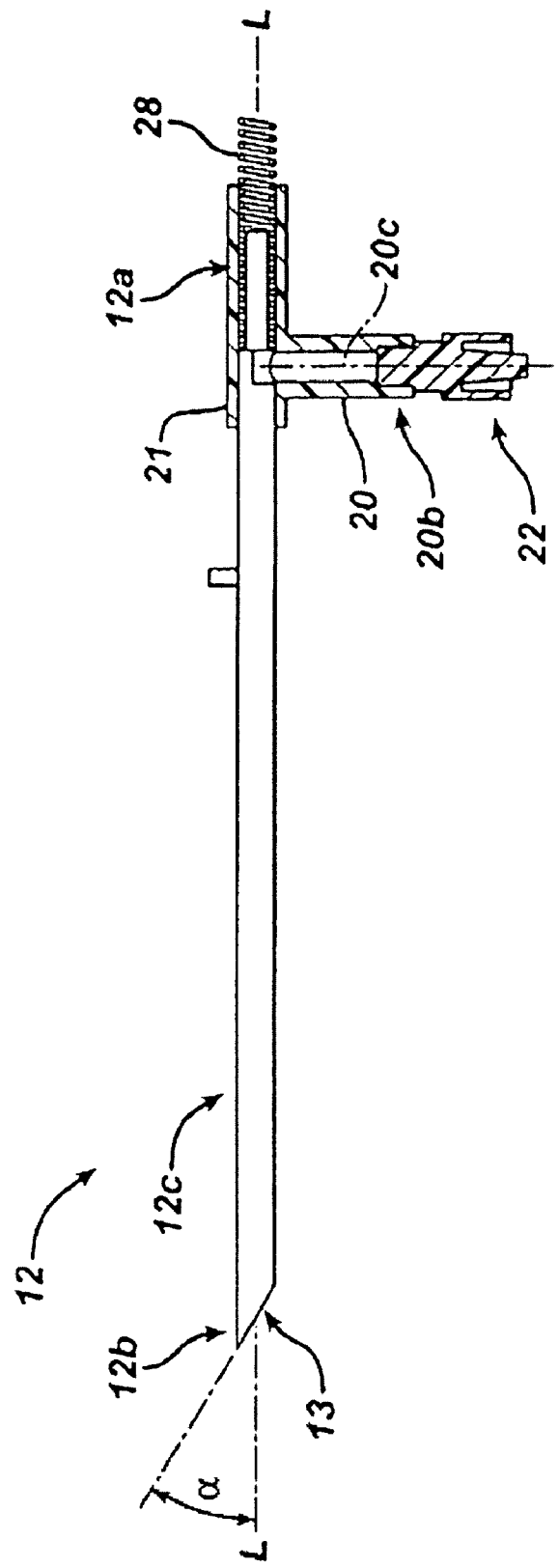
FIG. 2B is a cross-sectional view of the outer tube shown in FIG. 2A.

The outer tube 12 of the device 10, which is shown in more detail in FIGS. 2A and 2B, can have virtually any shape, size, and configuration. In the illustrated embodiment, the outer tube 12 has a generally elongate cylindrical shape and includes proximal and distal ends 12a, 12b with an inner lumen 12c extending therebetween. The proximal end 12a of the outer tube 12 can be open or closed, but it is preferably adapted to connect to a driver mechanism, as will be discussed below. The distal end 12b of the outer tube 12 is at least partially open and it can be adapted to rest against a tissue surface. The distal end 12b can further have a shape that is configured to provide a seal between the inner lumen 12c of the outer tube 12 and a tissue surface. As shown in FIG. 2B, the distal end 12b of the outer tube 12 is disposed at an angle .alpha. with respect to a longitudinal axis L of the device 10. While the angle .alpha. can vary, in an exemplary embodiment the distal end 12b is angled in the range of about 30.degree. to 70.degree., and more preferably at about 40.degree. with respect to the axis L. In use, the seal created between the distal end 12b and the tissue surface is particularly advantageous in that it will prevent foreign matter from entering the inner lumen 12c of the outer tube 12. While an angled distal end 12b is preferred, the distal end 12b of the outer tube 12 can have a variety of other configurations, and it can optionally include other features to facilitate placement on and/or a sealed connection with a tissue surface. By way of non-limiting example, the edge wall on the distal end 12b of the outer tube 12 can include surface features, such as ridges 13, formed thereon to facilitate the secure positioning of the outer tube 12 on a tissue surface. A person skilled in the art will appreciate that other techniques can be used to help maintain the position of the outer tube 12 on a tissue surface.

In another embodiment, the outer tube 12 can include a sidearm 20 for mating the device 10 to a tissue collection device, or for otherwise allowing the tissue sample to be collected. The sidearm 20 is preferably disposed adjacent to the proximal end 12a of the device 10, and it preferably extends in a direction substantially transverse to the longitudinal axis L of the tube 12. The sidearm 20 can optionally be coupled to the outer tube 12 by a second tube 21 that extends around a portion of the outer tube 12 and that is attached to the sidearm 20. The sidearm 20 includes an inner lumen 20c that is in communication with the inner lumen 12c of the tube 12, such that all material flowing into the distal end 12b of the tube 12 and through the inner lumen 12c of the tube 12 will enter into the inner lumen 20c in the sidearm 20, rather than exit through the proximal end 12a of the outer tube 12. The distal end 20b of the sidearm 20 can include a connector 22 formed thereon for mating with an entry port formed in a tissue collection device, which will be discussed in more detail with respect to FIG. 6. The connector 22 can have virtually any configuration depending on the type of tissue collection device that the sidearm 20 is adapted to mate to, but the connector 22 should preferably provide a fluid-tight seal between the sidearm 20 and the tissue collection device. The sidearm 20 can also be used to create a vacuum within the device 10 to draw tissue, and any fluid collected with the tissue, through the device 10. The vacuum source can be part of the tissue collection device, or optionally a separate vacuum source can be provided to mate with the sidearm 20. A person skilled in the art will appreciate that the vacuum source can couple to any portion of the outer tube 12, and that the outer tube can have a variety of other shapes, but it should at least be effective to retain a tissue sample therein.

The device 10 can also optionally include an outer housing 26 that extends around a portion of the proximal end 12a of the outer tube 12, and the sidearm 20, to facilitate handling of the device 10. The outer housing 26 can have virtually any shape and size, but it is preferably adapted to fit within a user's hands. In an exemplary embodiment, the outer housing 26 can include a rotating member 26a formed on a distal portion thereof for allowing rotation of the outer tube 12. As shown, the rotating member 26a is rotatably coupled to the housing 26, and it is positioned around and attached to the outer tube 12. As a result, the rotating member 26a can be used to control the position of the distal end 12b of the outer tube 12, thereby facilitating the proper placement of the distal end 12b of the outer tube 12 on a tissue surface. The rotating member 26a is preferably rotatable in a controlled fashion, rather than freely rotatable, such that the position of the outer tube 12 can be maintained during use.

Referring back to FIG. 1B, the device 10 further includes an inner shaft 14 that is disposed within and extends through the outer tube 12. The inner shaft 14 can also have a variety of shapes and sizes, but it is preferably a generally elongate cylindrical member having a proximal end 14a and a distal end 14b. The proximal end 14a of the shaft 14 can extend out of the proximal end 12a of the outer tube to couple to a driver mechanism 22 that is effective to rotate the shaft 14. Virtually any driver mechanism 22 can be used to rotate the shaft 14. As shown in FIG. 1A, and partially shown in FIG. 1B, the driver mechanism 22 is in the form of a motor (not shown) that is disposed within a housing. The motor, e.g., a drill or electric motor system, is effective to rotate the shaft 14. The driver mechanism 22 is preferably only mated to the shaft 14 such that the driver mechanism 22 is movable with the shaft 14 between the proximal and distal positions. In an exemplary embodiment, the motor is preferably operated at a speed that is in the range of about 100 rpm to 5000 rpm. Relatively low operating speeds are preferred to reduce the risk of causing damage to the tissue sample. A person skilled in the art will appreciate that virtually any driver mechanism can be used, and that the speed of the driver mechanism can vary depending on the intended use.

The proximal end 14a of the shaft 14 also includes a trigger mechanism 24 that is effective to move the shaft 14 between the proximal and distal positions. While the trigger mechanism 24 can have a variety of configurations, FIGS. 1A and 1B illustrate a trigger mechanism 24 coupled to the outer housing 26 that is disposed around a portion of the outer tube 12. The trigger mechanism 24 is pivotably disposed within the outer housing 26, and it is coupled to the driver mechanism 22 by a pull rod 25. As a result, when the trigger mechanism 24 is actuated, e.g., using one's finger, the trigger 24 rotates the pull rod 25 to pull the driver mechanism 22 in a distal direction, thereby causing the driver mechanism 22 to move the shaft 14 to the distal position. The shaft 14 preferably moves a distance sufficient to allow only a portion of the distal end 14b of the shaft to extend out of the outer tube 12, as will be discussed in more detail below.

In order to allow the shaft 14 to return to the proximal position after the trigger mechanism 24 is actuated, the device 10 can include a biasing element that is effective to bias the shaft 14 to the proximal position. The biasing element can have a variety of configurations, such as, for example, a spring 28, and it can be coupled to the trigger mechanism 24, the driver mechanism 22, and/or the shaft 14. As shown in FIGS. 1B-2B, the spring 28 is disposed around the proximal end 14a of the shaft 14, and it is positioned just proximal to the proximal end 12a of the outer tube 12. A portion of the spring 28 can optionally be disposed within a second tube 21 which extends around the proximal end 12a of the outer tube 12 to mate the sidearm 20 to the outer tube 12.

In use, the spring 28 is compressed between the driver mechanism 22 and the outer tube 12, thereby creating a biasing force that is effective to push the driver mechanism 22, as well as the inner shaft 14, back into the proximal position. The spring 28 is also effective to create a hard stop between the driver mechanism 22 and the outer tube 12, thereby limiting the distance that the inner shaft 14 can extend from the distal end 12b of the outer tube 12. In an exemplary embodiment, the shaft 14 moves a distance, between the proximal and distal positions, that is in the range of about 1 mm to 5 mm, and more preferably about 3 mm. A person skilled in the art will appreciate that a variety of other techniques can be used to move the shaft 14 between the proximal and distal positions.

Figure 3A:
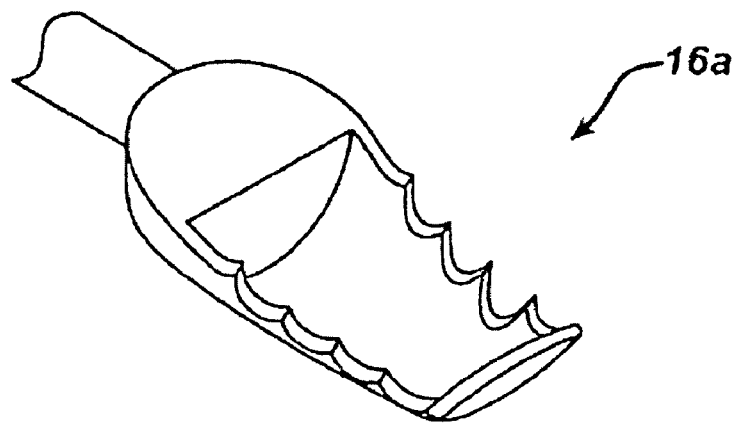
FIG. 3A illustrates one embodiment of a harvesting tip of an inner shaft for use with a tissue extraction and maceration device in accordance with the present invention.
Figure 3B:
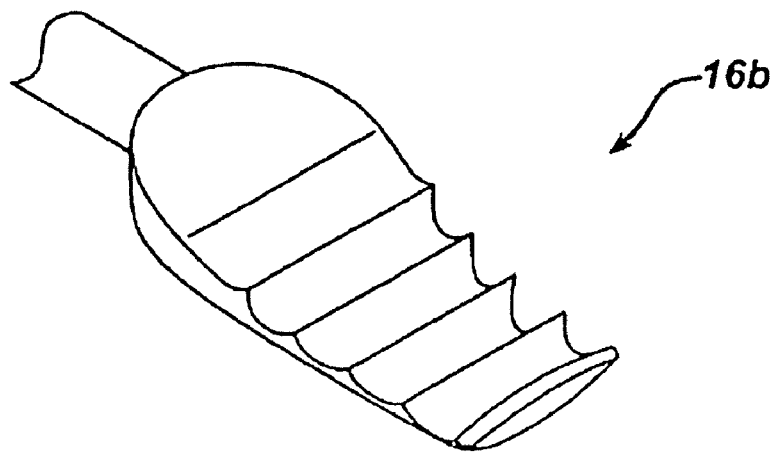
FIG. 3B illustrates another embodiment of a harvesting tip of an inner shaft for use with a tissue extraction and maceration device in accordance with the present invention.
Figure 3C:
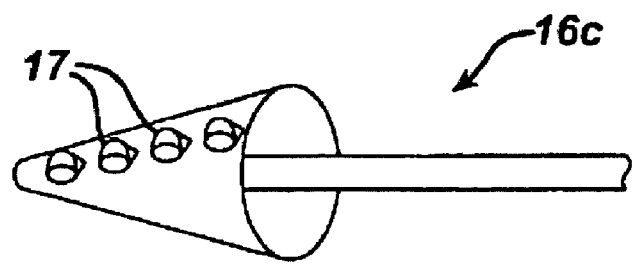
FIG. 3C illustrates yet another embodiment of a harvesting tip of an inner shaft for use with a tissue extraction and maceration device in accordance with the present invention.
Figure 3D:
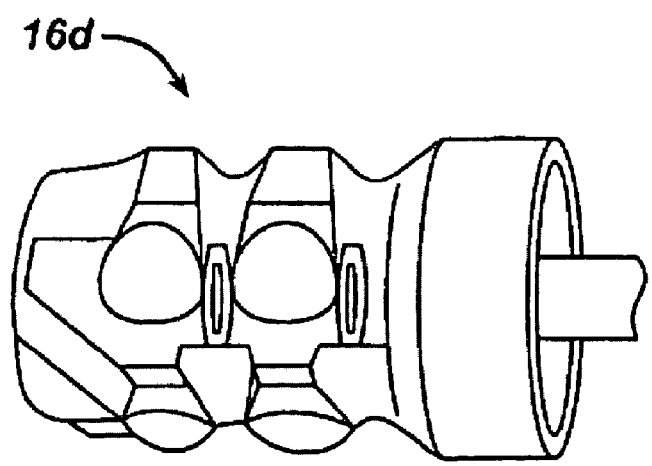
FIG. 3D illustrates yet another embodiment of a harvesting tip of an inner shaft for use with a tissue extraction and maceration device in accordance with the present invention.

The distal end of the inner shaft 14, which is adapted to extend from outer tube 12 when moved into the distal position, preferably includes a tissue harvesting tip 16 that is adapted to retrieve a tissue sample. The tissue harvesting tip 16 can have a variety of configurations, but it is preferably adapted to retrieve a viable tissue sample without tearing or otherwise causing damage to the tissue. More particularly, the tissue harvesting tip 16 should allow for the rapid removal of cleanly cut tissue, rather than crushed or torn tissue. By way of non-limiting example, FIGS. 3A-3D illustrate several embodiments of tissue harvesting tips 16a-d that can be used. FIGS. 3A and 3B each illustrate a substantially semi-cylindrical tissue harvesting tip 16a, 16b having a scalloped parameter that is effective to cut into tissue upon rotation of the shaft 14. In FIG. 3A, the tissue harvesting tip 16a is substantially hollow to obtain a larger tissue sample, while in FIG. 3B the tissue harvesting tip 16b is substantially solid and the scallops extend across the surface to form ridges on the harvesting tip 16b. FIGS. 3C and 3D illustrate alternative embodiments of tissue harvesting tips 16c, 16d. In particular, FIG. 3C illustrates a hollow cone-shaped member having several cutting teeth 17 formed around and protruding above an outer surface of the cone-shaped member. The cutting teeth 17 function similar to a cheese grater in that they penetrate the tissue to remove several small tissue samples which are collected inside the hollow cone. FIG. 3D illustrates a tissue harvesting tip 16d that is very similar to the tissue harvesting tip 16c illustrated in FIG. 3C, but that has a substantially cylindrical shape and that includes a substantially flattened distal end.

While the harvesting tip 16 used with the device 10 can have a variety of configurations, shapes, and sizes, the harvesting tip 16 is preferably effective to retrieve a predetermined amount of tissue. In an exemplary embodiment, the predetermined volume of tissue, per tissue sample, retrieve by the harvesting tip 16 is in the range of about 0.5 cm.sup.3 to 1.5 cm.sup.3, and more preferably about 0.9 cm.sup.3. A person skilled in the art will appreciate that a variety of tissue harvesting tips can be used with a device in accordance with the present invention, and that FIGS. 3A-3D merely illustrate exemplary embodiments.

Figure 4A:
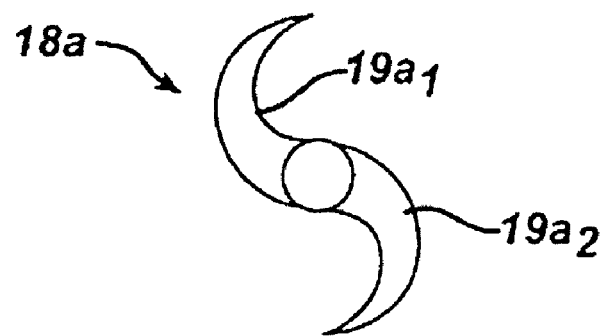
FIG. 4A illustrates one embodiment of a cutting member for use with a tissue extraction and maceration device in accordance with the present invention.
Figure 4B:
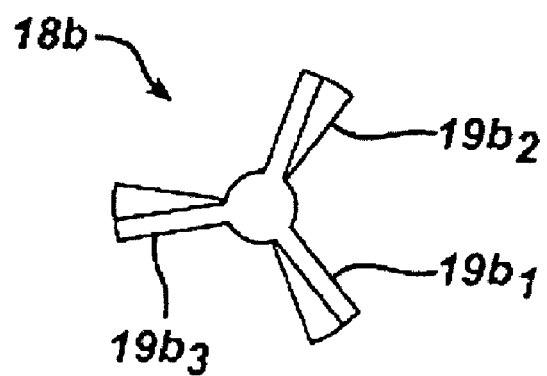
FIG. 4B illustrates another embodiment of a cutting member for use with a tissue extraction and maceration device in accordance with the present invention.
Figure 4C:
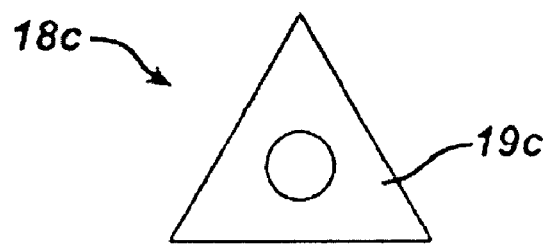
FIG. 4C illustrates yet another embodiment of a cutting member for use with a tissue extraction and maceration device in accordance with the present invention.
Figure 4D:
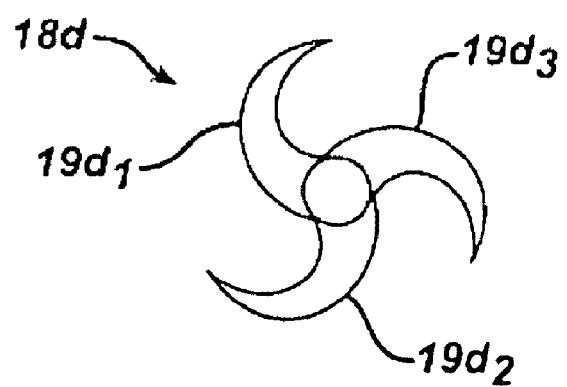
FIG. 4D illustrates yet another embodiment of a cutting member for use with a tissue extraction and maceration device in accordance with the present invention.
Figure 4E:
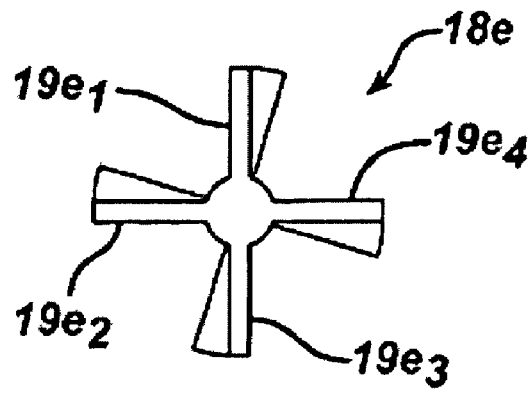
FIG. 4E illustrates yet another embodiment of a cutting member for use with a tissue extraction and maceration device in accordance with the present invention.
Figure 4F:
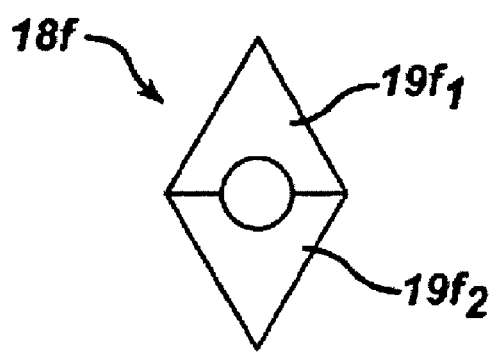
FIG. 4F illustrates yet another embodiment of a cutting member for use with a tissue extraction and maceration device in accordance with the present invention.

The distal end 14b of the shaft 14 can also include a cutting member 18, which is preferably disposed around the shaft 14 at a positioned just proximal to the tissue harvesting tip 16. The cutting member 18 can have a variety of shapes and sizes, but it is preferably effective to macerate the tissue sample excised by the tissue harvesting tip 16. Similar to the tissue harvesting tip 16, the cutting member 18 should be effective to cut, rather than tear, the tissue to allow a viable tissue sample to be obtained. By way of non-limiting example, FIGS. 4A-4F illustrate several embodiments of cutting members 18a-18f that can be used with a device in accordance with the present invention. In general, each cutting member 18a-18f includes one or more blades 19 formed thereon having a particular shape, such as a rectangular shape, a curved shape, a triangular shape, a square shape, or an irregular shape. More particularly, FIG. 4A illustrates a cutting member 18a having two curved or C-shaped blades 19a.sub.1, 19a.sub.2 formed thereon; FIG. 4B illustrates a cutting member 18b having three substantially triangular shaped blades 19b.sub.1, 19b.sub.2, 19b.sub.3 extending from the shaft and positioned equidistant from one another; FIG. 4C illustrates a single triangular shaped blade 19c that forms a cutting member 18c; FIG. 4D illustrates a cutting member 18d, similar to cutting member 18a, but having three curved or C-shaped blades 19d.sub.1, 19d.sub.2, 19d.sub.3, formed thereon; FIG. 4E illustrates a cutting member 18e, similar to cutting member 18b, but having four substantially triangular shaped blades 19b.sub.1, 19b.sub.2, 19b.sub.3, 19b.sub.4 extending from the shaft and positioned equidistant from one another; and FIG. 4F illustrates a cutting member 18f having two triangular blades 19f.sub.1, 19f.sub.2 formed thereon. While a variety of cutting elements 18 are illustrated, in an exemplary embodiment, the cutting element is effective to macerate tissue into particles having a diameter in the range of about 0.7 mm to 1.3 mm, and more preferably about 1.0 mm.

Figure 5:
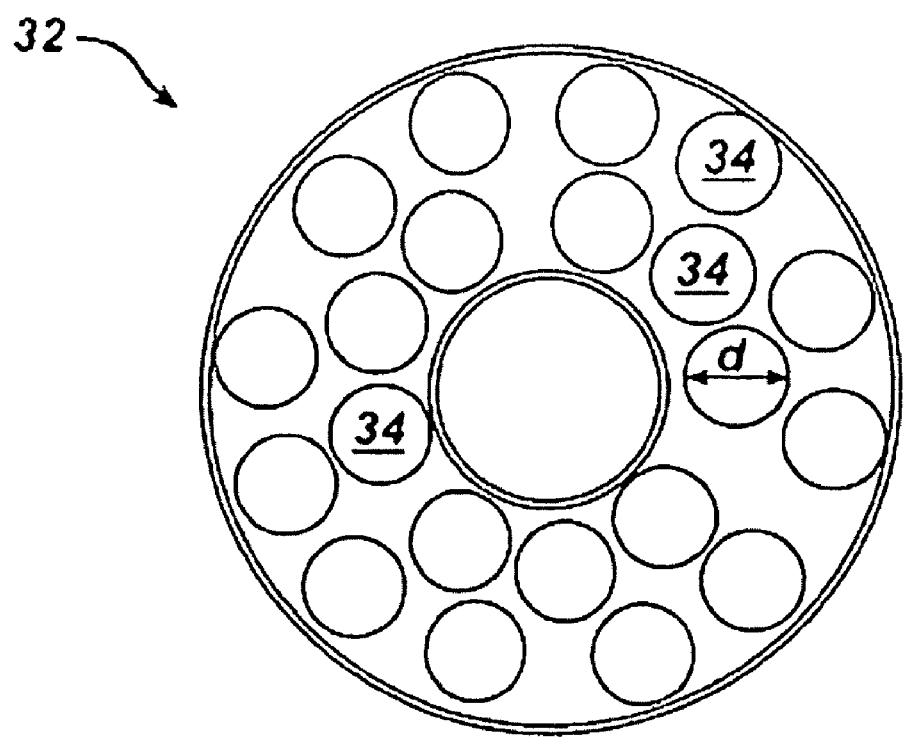
FIG. 5 illustrates one embodiment of a sizing screen for use with a tissue extraction and maceration device in accordance with the present invention.

The device 10 can also optionally include a sizing screen 32, as shown in FIG. 5, that is adapted to control the size of the tissue particles that are allowed to pass through the outer tube 12. The sizing screen 32 is preferably disposed just proximal to the cutting member 18, and it can include several openings 34 formed therein which have a size that permits tissue particles having a size less than the size of the openings 34 to pass therethrough. The openings 34 can vary in shape and size, but in an exemplary embodiment the openings 34 have a diameter d in the range of about 0.7 mm to 1.3 mm, and more preferably about 1.0 mm. As a result, only tissue particles having a size smaller than the size of the openings 34 will be allowed to pass through the sizing screen 32. The remaining tissue particles, which have a size greater than the size of the openings 34, will continue to be excised by the cutting member 18 until they are small enough to pass through the openings 34. To ensure that all of the tissue sample is excised to the appropriate size, the cutting member 18 and the sizing screen 32 are preferably positioned substantially close to one another so that tissue particles being held (preferably by a vacuum force) against the sizing screen 32 will come into contact with the cutting member 18. In another embodiment, the sizing screen 32 can facilitate excising of the tissue sample. In particular, each opening can have an upstream edge that is effective to cut tissue having a size greater than the circumference of the openings.

Figure 7A:
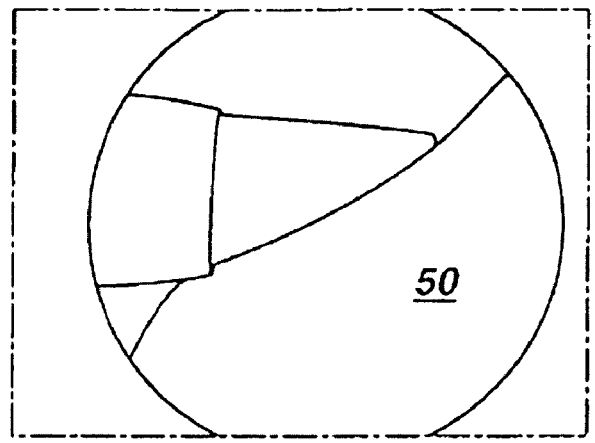
FIG. 7A illustrates a tissue extraction and maceration according to the present invention positioned on a tissue surface.
Figure 7B:
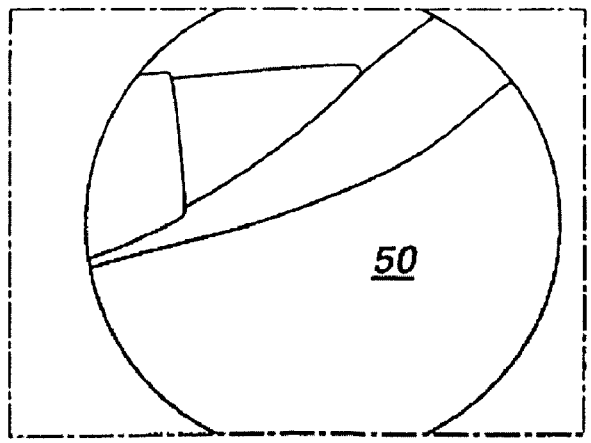
FIG. 7B illustrates the tissue surface having a tissue sample removed therefrom using a tissue extraction and maceration device according to the present invention.

In use, the device 10 is connected to a vacuum source (preferably via the sidearm 20) that is effective to create a vacuum within the inner lumen 12c of the outer tube 12, and the distal end 12b of the outer tube is positioned against tissue surface 50, as shown in FIG. 7A. The motor 22 is activated to rotate the shaft 14, and the trigger 24 is then squeezed to advance the motor 22 and the shaft 14 in a distal direction. As a result, the tissue harvesting tip 16 will extend out of the distal end 12b of the outer tube 12 and into the tissue. Since the shaft 14 is rotating, the tissue harvesting tip 16 will rotate to excise a tissue sample. As the trigger 24 is released, the biasing element 28 causes the shaft 14 to return to the proximal position. The trigger 24 is preferably only actuated once to cause the shaft to rapidly advance into the tissue to obtain a tissue sample. Once the sample is obtained, the vacuum force draws the tissue sample toward the sizing screen 32, where in the rotating cutting member 18 macerates the tissue. Once the macerated particles are small enough to fit through the openings 34 in the sizing screen 32, the particles are drawn through the inner lumen 12b of the outer tube 12, and preferably through the inner lumen 20c in the sidearm 20. Additional samples of tissue can be taken by repositioning the distal end 12b of the outer tube 12 on a tissue surface and actuating the trigger 24 to obtain another sample. FIG. 7B illustrates a tissue surface 50 having a tissue sample removed therefrom, and having the distal end 12b of the outer tube 12 repositioned to obtain a second sample.

Figure 6:
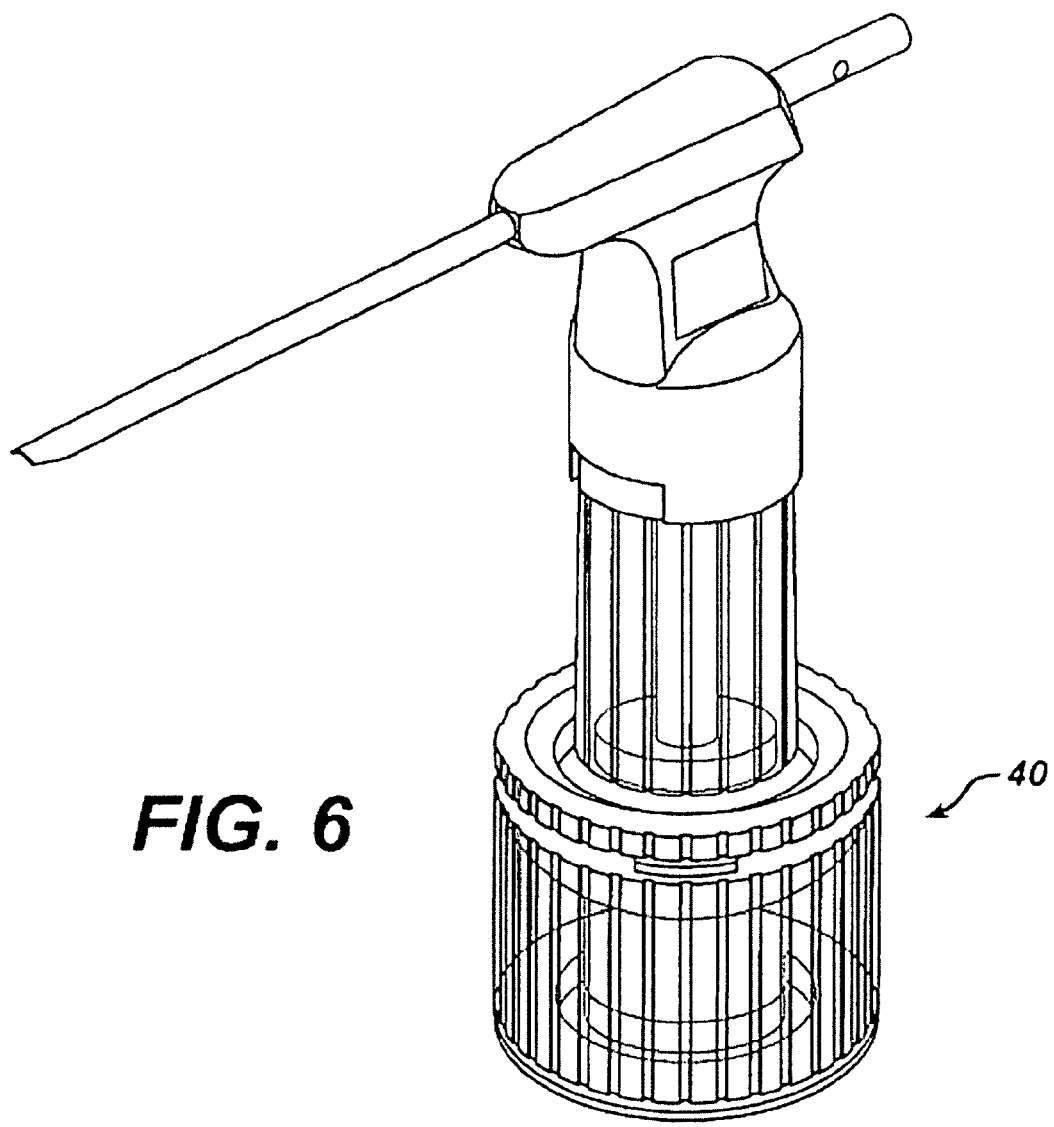
FIG. 6 illustrates the tissue extraction and maceration device shown in FIG. 1A mated to a tissue collection device according to another embodiment of the present invention.

As previously indicated, the tissue sample can be collected into a tissue collection device. While virtually any tissue collection device can be used, FIG. 6 illustrates an exemplary embodiment of a tissue collection device 40. The tissue collection device 40 generally includes a housing having an inner chamber with a tissue scaffold disposed therein. The device 40 is effective to deposit the macerated sample onto the tissue scaffold, and to collect and excess fluid obtained with the tissue sample. The device 40 is described in more detail in U.S. patent application Ser. No. 10/402,266, entitled "Tissue Collection Device and Methods," filed on Mar. 28, 2003, (now published as US Patent Publication No. 2004/0193071) and incorporated herein by reference in its entirety. The combination of the device 10 and the tissue collection device 40 is particularly advantageous in that it allows a tissue sample to be excised, macerated, and deposited onto a tissue scaffold in a single step.

FIGS. 8A-11B illustrate another exemplary embodiment of a device for tissue extraction and collection 90, which can generally include a handle housing 100 and an outer tube 102 extending distally therefrom and optionally including a beveled tip 104. A tissue harvesting tip 106 can be positioned at the distal end 108 of an inner shaft 110 extending through the outer tube 102 (which is shown with more detail in the exploded view of the cutter assembly 500 in FIG. 12). The inner shaft 110 can extend through the outer tube such that at least part of the tissue harvesting tip 106 is exposed. At its proximal end 118, the inner shaft 110 can be coupled via drive coupling 111 to a drive mechanism 112, such as a motor 114 and a power transfer assembly 116. A portable electrical power source, such as a battery pack 120, or other power source can supply power to the motor 114 under the control of a switch 122 on the handle housing 100. The drive mechanism 112 can be effective to rotate the inner shaft 110 and the tissue harvesting tip 106 such that the tissue harvesting tip 106 excises tissue to which it is applied. In some embodiments, the drive mechanism 112 can be adapted to stall or otherwise stop when the tissue harvesting tip 106 is applied to certain tissue, for example, bone, so as to do "selective harvesting" and reduce contamination.

A mounting tube 126 can be disposed around a portion of the outer tube 102 (as shown, it can be a portion of the outer tube 102) and can provide a coupling between the outer tube 102, the inner shaft 110, the drive mechanism 112, and a transfer tube 124. The transfer tube 124 can be in communication with a lumen formed in the inner shaft 110. As will be described in more detail below, in many embodiments the inner shaft 110 and the drive coupling 111 can be adapted to allow excised tissue and any fluid therewith to be evacuated therefrom (while the inner shaft 110 is rotating, in many embodiments) and into the transfer tube 124.

Figure 9A:
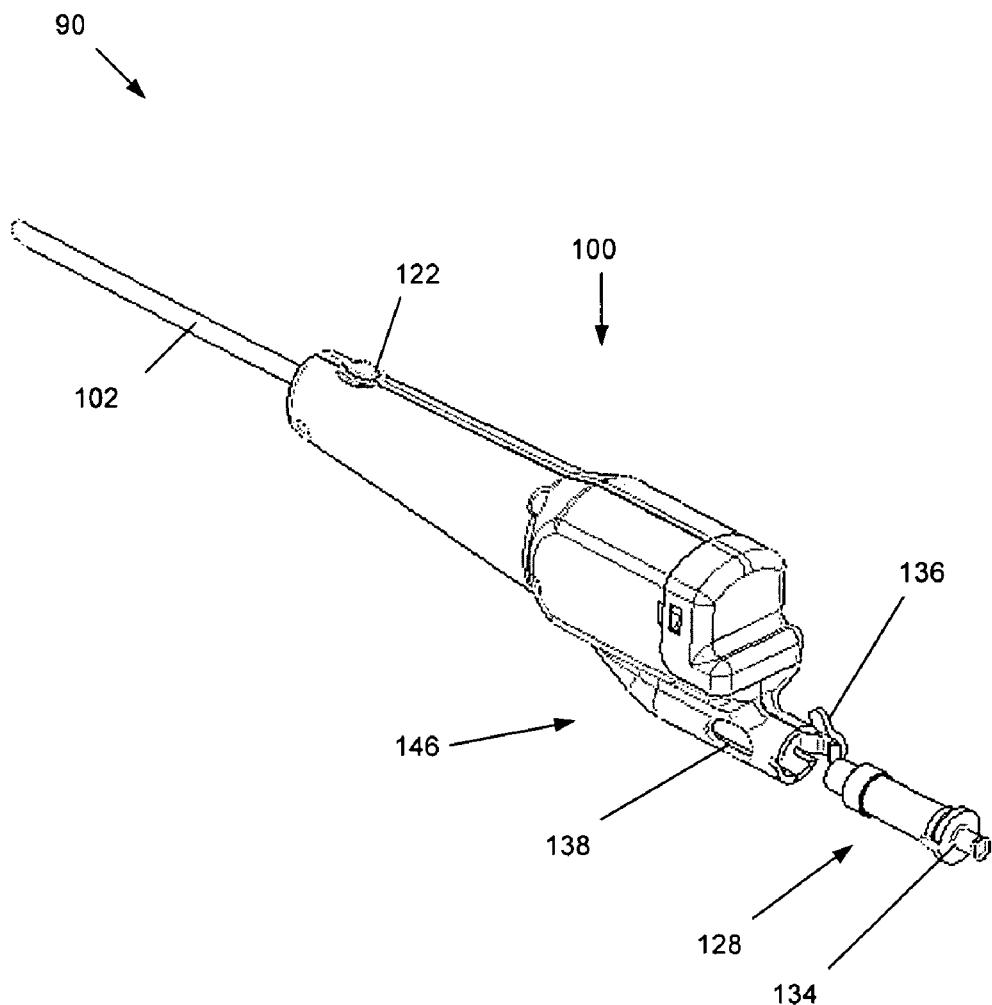
FIG. 9A is a rear perspective view of the tissue extraction and collection device shown in FIG. 8A, with a tissue collection device removed therefrom.
Figure 9B:
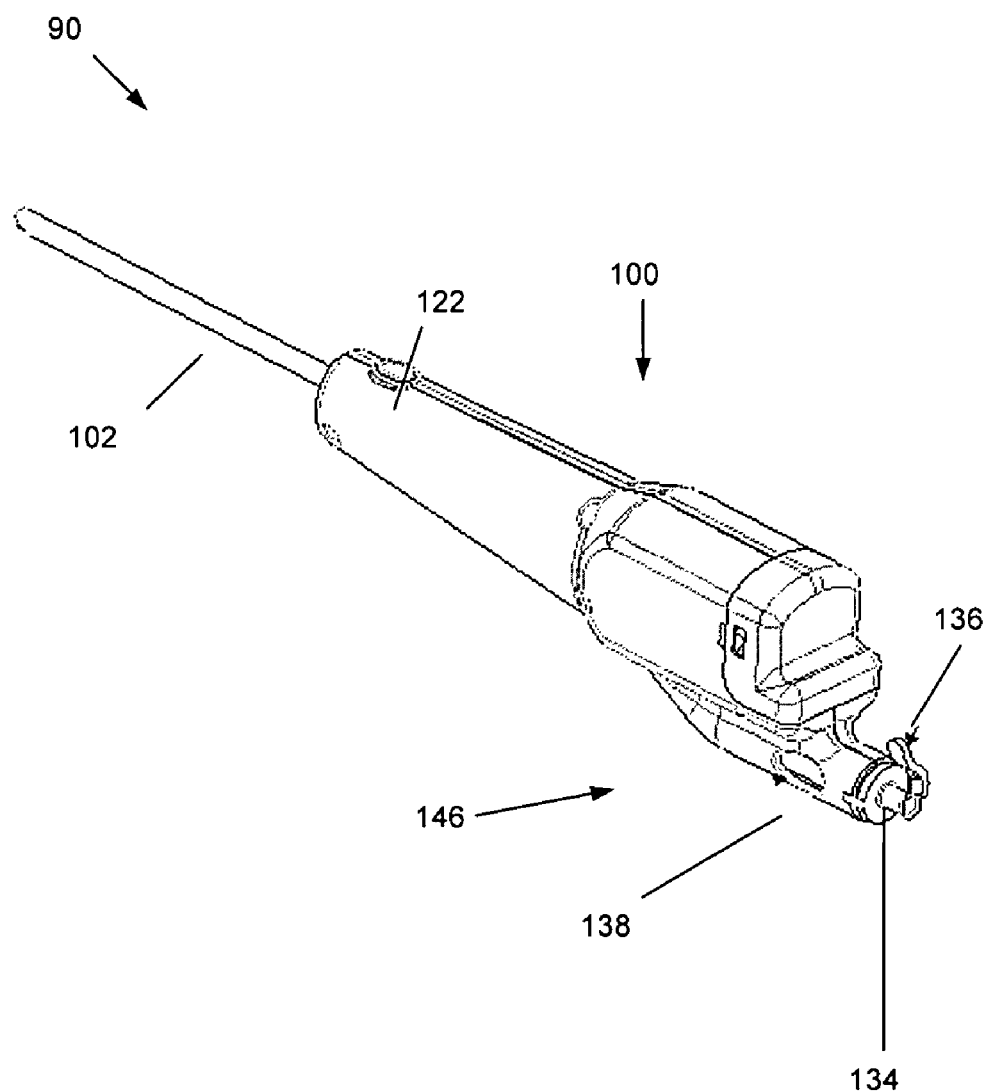
FIG. 9B is a rear perspective view of the tissue extraction and collection device shown in FIG. 8A showing the tissue collection device disposed in the handle housing.
Figure 9C:
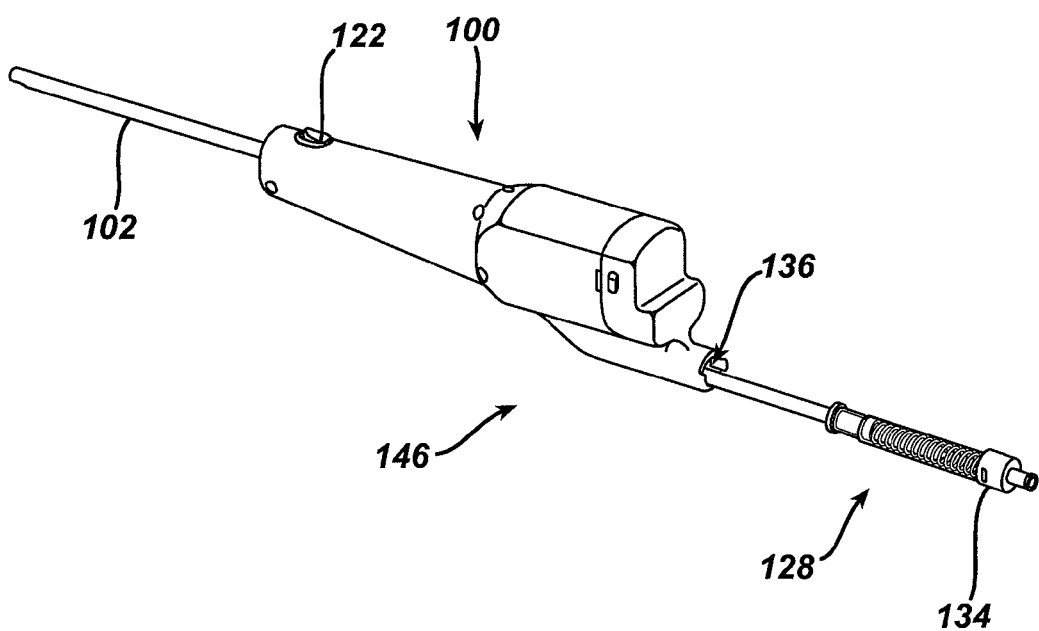
FIG. 9C is a rear perspective view of the tissue extraction and collection device shown in FIG. 8A with the tissue collection device in an extended position.
Figure 10:
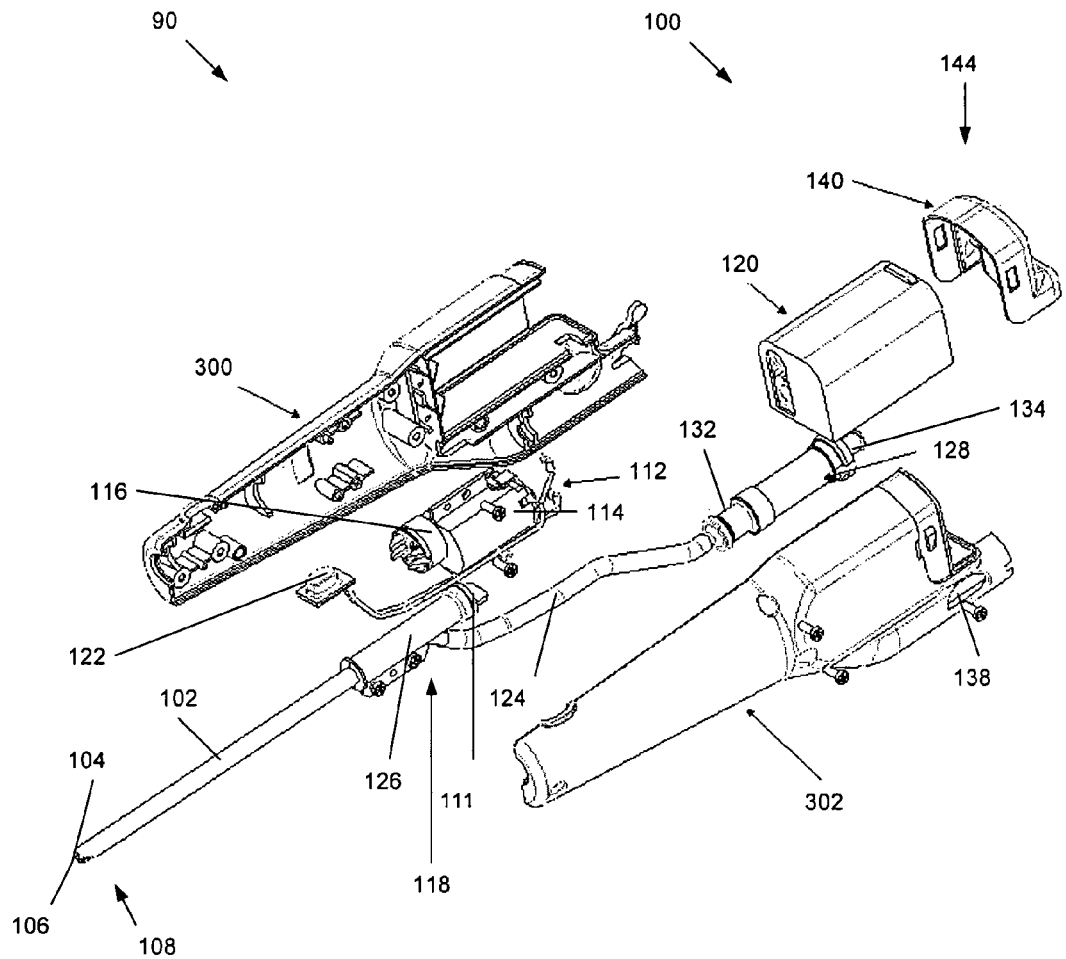
FIG. 10 is an exploded view of the tissue extraction and collection device shown in FIG. 8A.
Figure 11A:
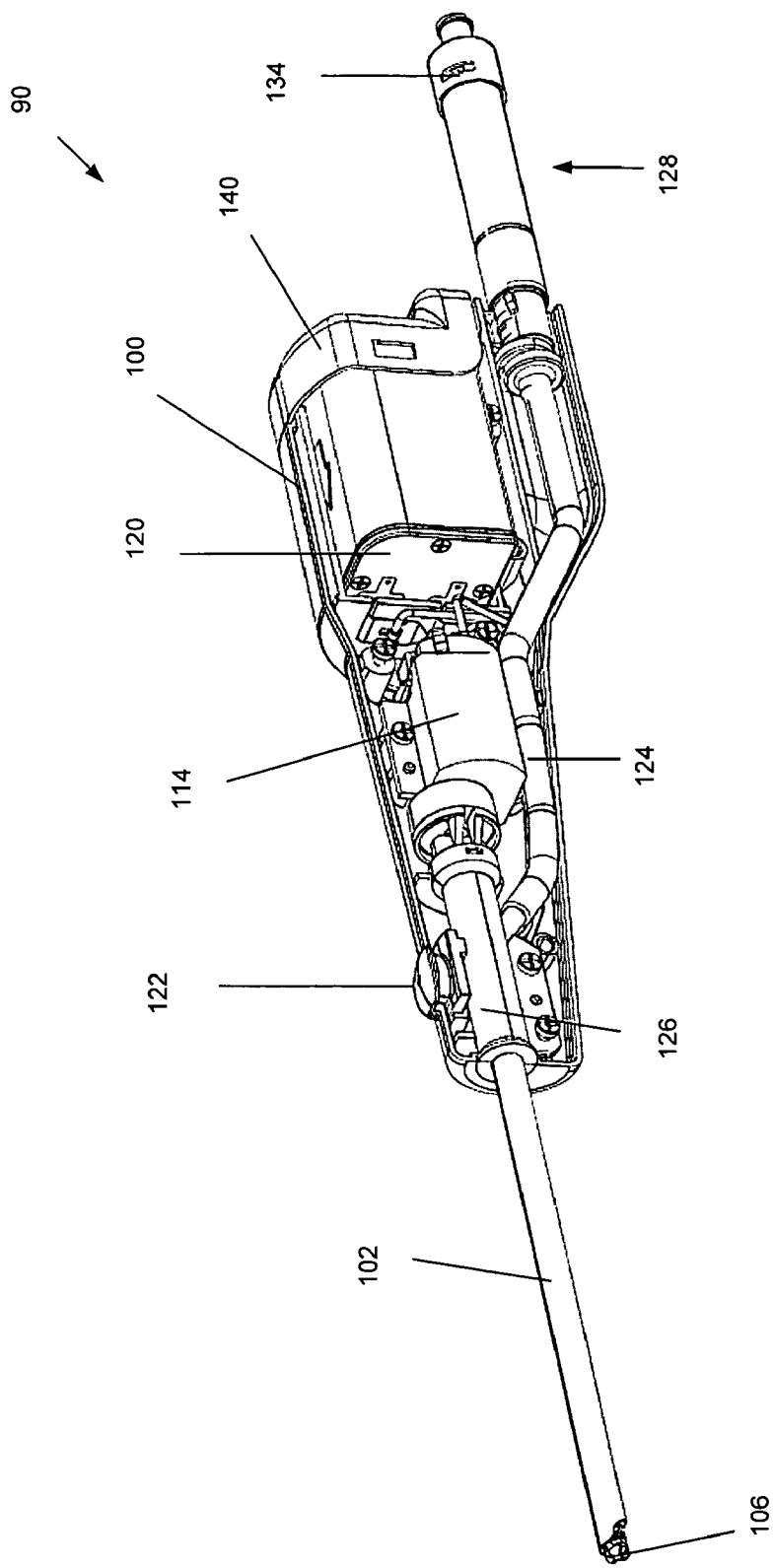
FIG. 11A is a cutaway view of the tissue extraction and collection device shown in FIG. 8A.
Figure 11B:
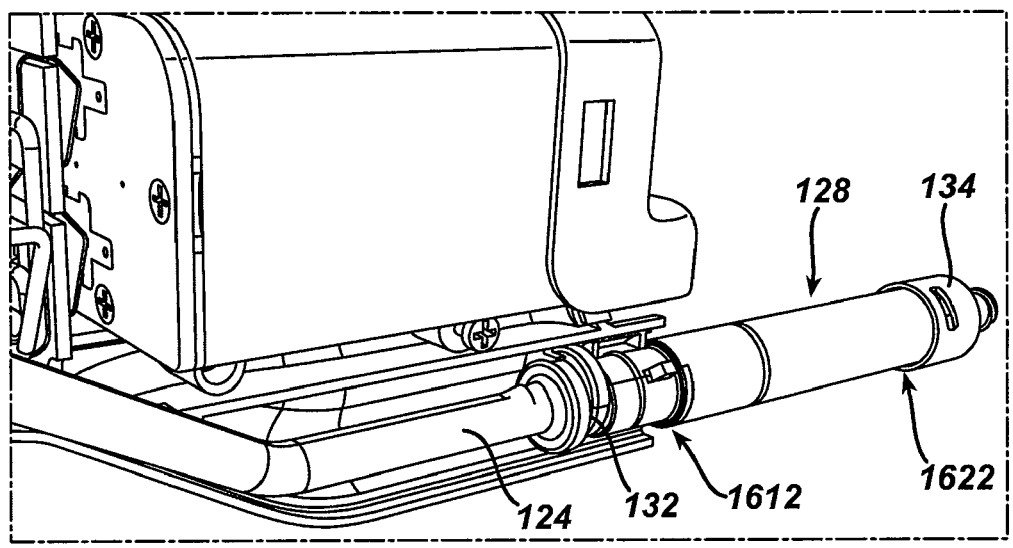
FIG. 11B is cutaway view of a portion of the tissue extraction and collection device shown in FIG. 8A illustrating the tissue collection device coupled to the tissue extraction and collection device.

The transfer tube 124 can be coupled to a tissue collection device 128, which as shown in FIGS. 9A-11B can be located in the handle housing 100. The tissue collection device 128 can include a container 130 with an inlet 1612 and an outlet 1622. An inlet fitting 132 can provide a coupling between the inlet 1612 and the transfer tube 124, while an outlet fitting 134 can provide a coupling between the outlet 1622 and an external vacuum source. In use, the tissue collection device 128 can collect the excised tissue within the container 130 while allowing fluid to pass through to the vacuum source. As will be described in more detail below, in many embodiments the tissue collection device 128 can include a mechanism to indicate and/or quantify the amount of tissue collected therein, for example visually through a sighting port 138 or in other ways. In some embodiments, the tissue collection device 128 can be separated from the handle housing 100, as shown in FIGS. 9A and 11B, to remove the collected tissue. The tissue collection device 128 can also be extended from the handle housing 100 without disconnecting it from the device 90, as shown in FIG. 9C, which can be advantageous for more detailed viewing of the contents of the tissue collection device 128, or other functions. The collected tissue can be deposited on a tissue scaffold, used to culture cells, or used in any of a wide range of applications.

Figure 8A:
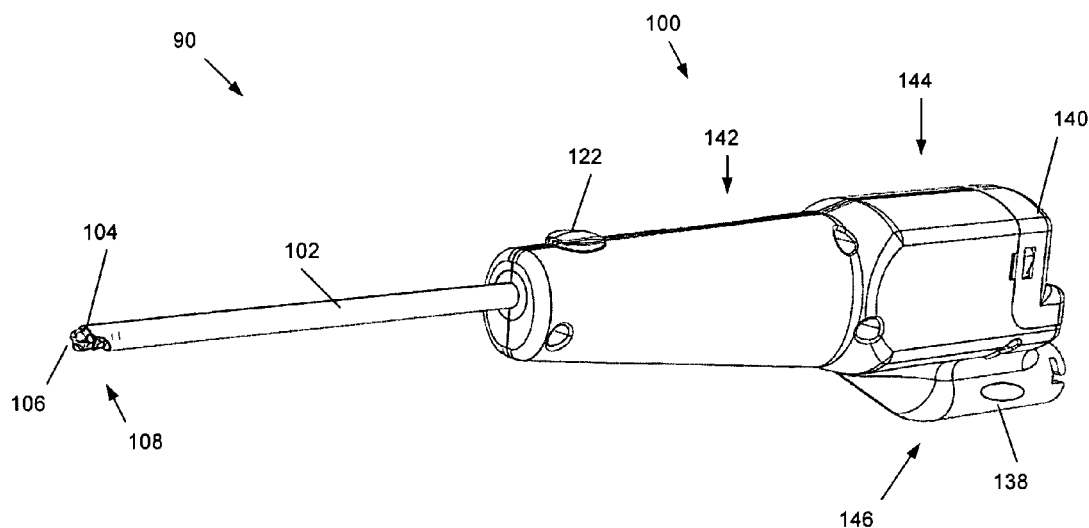
FIG. 8A is a front perspective view of another exemplary embodiment of a tissue extraction and collection device having a handle housing with an outer tube extending distally therefrom and a tissue harvesting tip at its distal end.
Figure 8B:
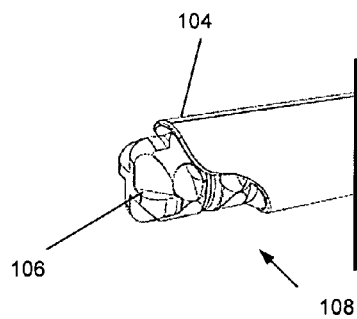
FIG. 8B is a detail view of the tissue harvesting tip at the distal end of the device shown in FIG. 8A.

Turning to FIG. 8A, the handle housing 100 can have a wide variety of shapes, but as shown the handle housing 100 has a tapered portion 142 with an integrated switch 122 and a base portion 144, which can be sized to contain the battery pack 120. As shown, the tapered portion 142 can house the motor 114, while the base portion 144 can house the battery pack 120, although the location of components can vary. The handle housing 100 can also have a portion 146 that contains the tissue collection device 128 and which can have a sighting port 138 formed therein. A connection mechanism 136, as shown in FIGS. 9A and 9B, such as a luer fitting, a spring-loaded latch, or other latch, can be provided on the handle housing 100 for controllably retaining the tissue collection device 128 therein. As seen in FIG. 10, the handle housing 100 can be formed of multiple pieces, and more specifically of a right handle housing 300 and a left handle housing 302, which can then be assembled or joined, for example via screws, adhesive, etc. A cover 140 for the battery pack 120 can be integrated with the handle housing 100. In some embodiments, the cover 140 can be freely removable. In other embodiments, particularly in applications in which one-time or limited-time use of the device 90 is desired, the cover 140 can be adapted to be permanently latched (e.g., a one-way latch without a release) such that after installation of batteries or other power source the cover 140 must be broken in order to be opened, preventing a second installation of batteries. The handle housing 100 can be made of a variety of materials, including stainless steel, plastic, and/or virtually any biocompatible material, which can be used for any or all of the other components described herein as well. A person skilled in the art will appreciate that the handle housing 100 can have various other configurations, and the configuration can vary depending on the placement of the components housed therein.

Figure 12:
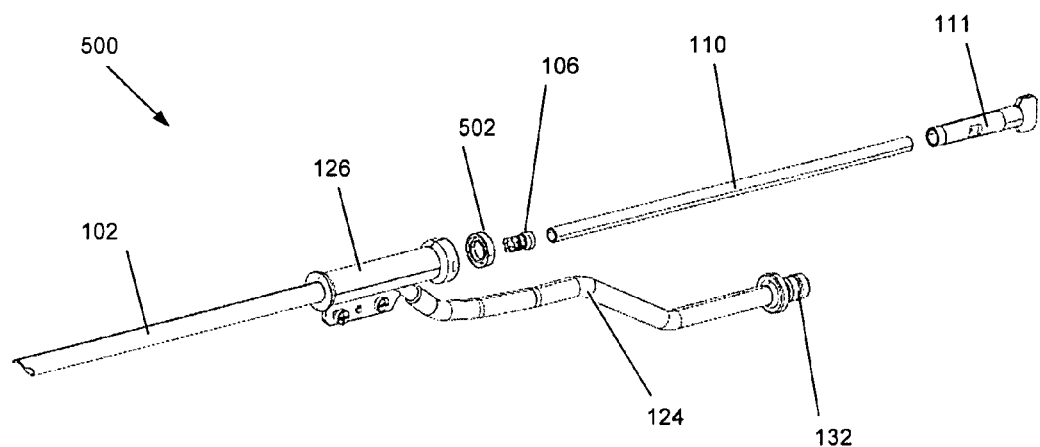
FIG. 12 is an exploded view of several components of the tissue extraction and collection device shown in FIG. 11A which can form a cutter subassembly.
Figure 13:
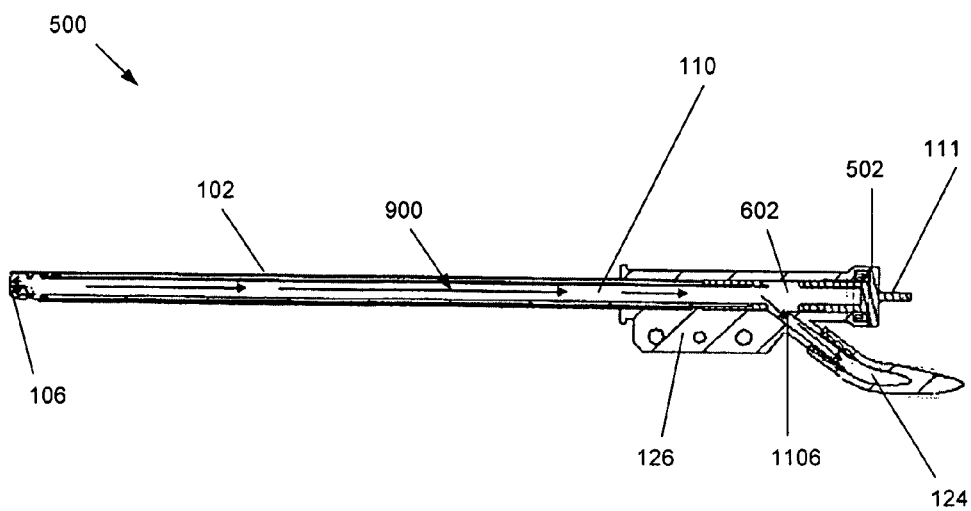
FIG. 13 is a side cross-sectional view of the cutter assembly shown in FIG. 12 with arrows showing exemplary tissue and/or fluid flow therethrough.

As previously mentioned, FIG. 12 illustrates an exemplary cutter subassembly 500, while FIG. 13 provides a cross-sectional view of the subassembly 500. In general, the cutter assembly 500 can include the outer tube 102, which as shown is coupled to the mounting tube 126 and which receives the inner shaft 110. A seal 502 can be provided to form a tight, e.g., fluid-tight, connection between the mounting tube 126 and the inner shaft 110 and/or the drive coupling 111. The mounting tube 126 can also provide a coupling to the transfer tube 124, which in turn can be coupled to the inlet fitting 132 of the tissue collection device 128.

Figure 14A:
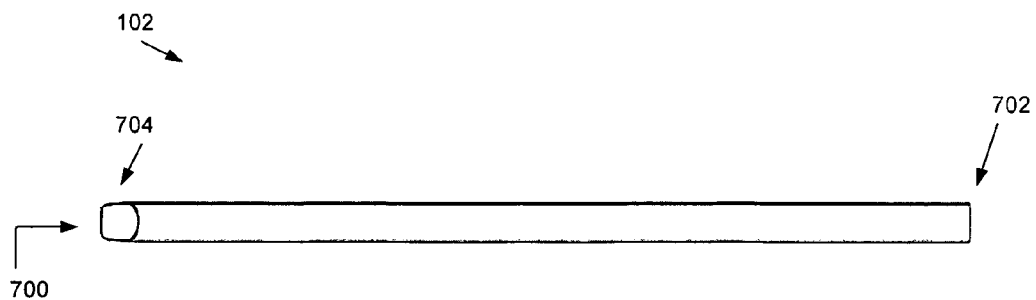
FIG. 14A is a bottom view of the outer tube shown in FIGS. 8A-11B.
Figure 14B:
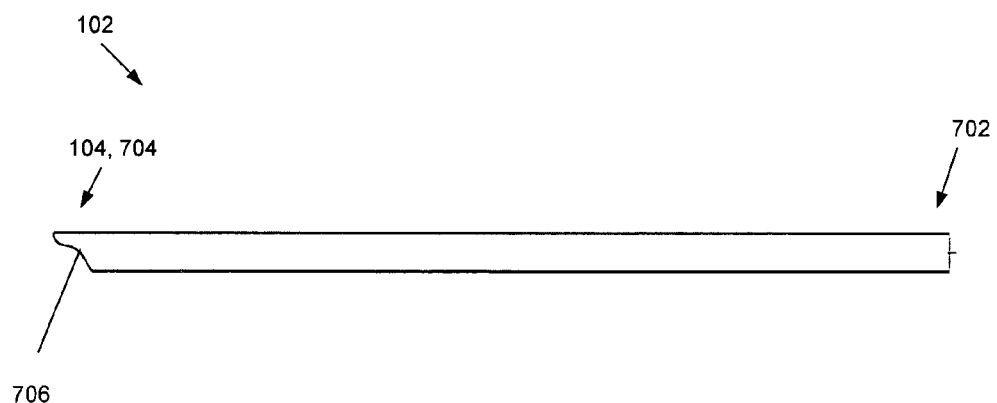
FIG. 14B is a side view of the outer tube shown in FIGS. 8A-11B.

FIGS. 14A and 14B show the outer tube 102 in more detail. The outer tube 102 can have a wide variety of configurations, but in the illustrated embodiment it is substantially cylindrical and includes a lumen 700 formed therein between proximal and distal ends 702, 704 thereof. As one skilled in the art will understand, the outer tube 102 need not be cylindrical and can be constructed in any of a wide range of cross-sectional shapes, e.g., rectangular, square, oval, and so on. In an exemplary embodiment, the distal end 704 of the outer tube has a beveled tip 104. The beveled tip 104 can be sized so as to cover a portion of the tissue harvesting tip 106, e.g., as a hood or protective cover, while exposing another portion of the tissue harvesting tip 106, as seen in the detail view of FIG. 8B. Such a configuration can be advantageous to facilitate the excision of tissue by one portion or side of the partially exposed tissue harvesting tip 106 without unwanted contact or damage by other portions of the tissue harvesting tip 106 (e.g., those covered by the covered surface). The beveled tip 104 also can be advantageous for creating a seal against tissue or otherwise accommodating tissue as the outer tube 102 is pressed against it, for example in embodiments in which the tissue harvesting tip 106 is retractable into the outer tube 102. As shown in FIG. 14B, the distal surface 706 of the beveled tip 104 can have an S-shaped profile. In other embodiments, the distal surface 706 of the beveled tip 104 can be linear, angular, concave, convex, or other shapes.

Figure 15A:
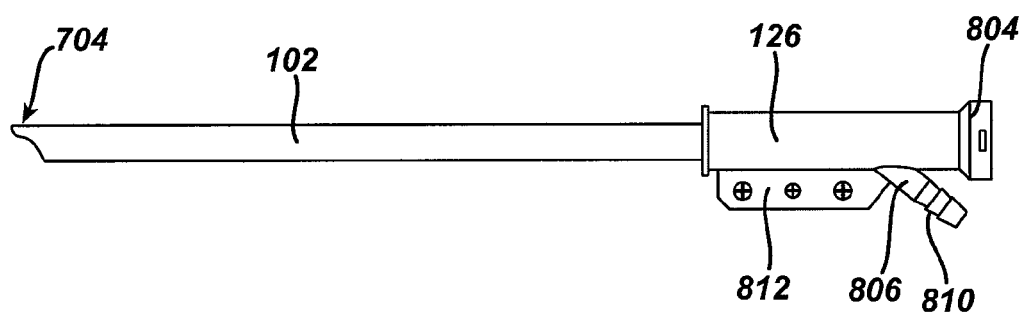
FIG. 15A is a side view of the outer tube and mounting tube shown in FIGS. 10-11B.
Figure 15B:
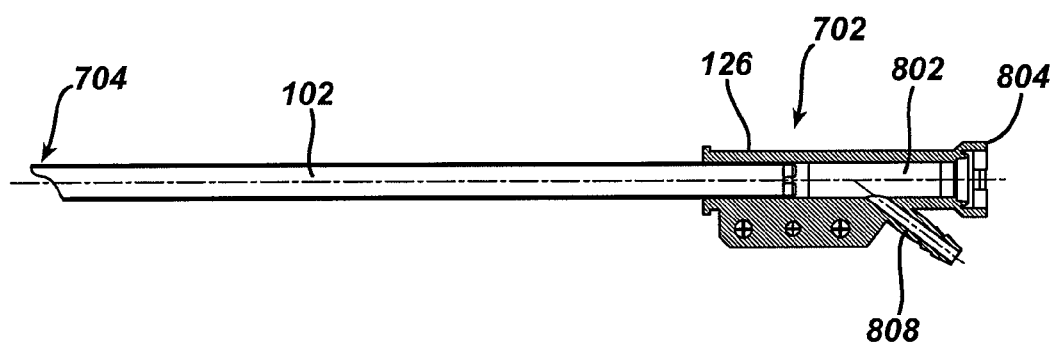
FIG. 15B is a cross-sectional view of the outer tube and mounting tube shown in FIGS. 10-11B.

As shown in FIGS. 15A and 15B, the mounting tube 126 can be coupled to the outer tube 102 at a proximal end 702 thereof. The mounting tube 126 can have a wide range of configurations. The mounting tube 126 can be formed as a single piece and coupled to the outer tube 102 with an interference fit, adhesive or screw means, etc., or in other embodiments, can be constituted by two or more pieces which can be joined, for example with screw plate 812. The mounting tube 126 can have a lumen 802 formed therein that is sized to accept the inner shaft 110. Proximal to the outer tube 102, the lumen 802 can widen under flange portion 804 to receive the drive coupling 111. A coupling 806 can extend from the longitudinal axis of the lumen 802 and can have a channel or lumen 808 formed therein. The exterior surface of the coupling 806 can include notches 810 to improve retention of the transfer tube 124 when placed thereon. The configuration of the transfer tube 124 can also vary widely, but in this embodiment as shown in FIGS. 11A and 11B, the transfer tube 124 is a flexible tubular member. The transfer tube 124 can be formed of a elastomeric material such as rubber or other polymer, or other materials. Alternatively, the transfer tube 124 can be rigid, or comprised of rigid segments, and seals can be provided where it interfaces with other components such as the coupling 806 on the mounting tube 126.

Figure 16:
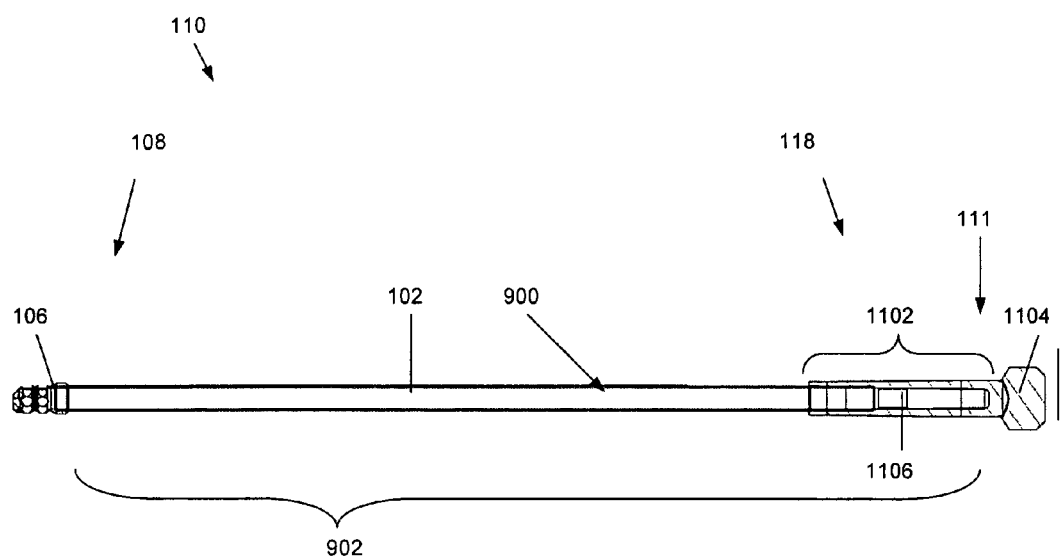
FIG. 16 is a side view of the inner shaft shown in FIG. 12 with a tissue harvesting tip at a distal end and a drive coupling at a proximal end.

FIG. 16 illustrates the inner shaft 110 with a tissue harvesting tip 106 at its distal end 108 and a drive coupling 111 at its proximal end 118. While the inner shaft can have a variety of configurations, as shown the inner shaft 110 is cylindrical in shape and sized to fit within the outer tube 102, and preferably sized to freely rotate therein. The inner shaft 110 can have an inner lumen 900 defined therein between its proximal and distal ends 118, 108, the lumen 900 extending into the drive coupling 111. As previously mentioned, the inner lumen 900 can receive excised tissue and fluid from the tissue harvesting tip 106, which is shown in more detail in FIG. 17. The tissue harvesting tip 106 can have a variety of configurations. In many embodiments, the tissue harvesting tip 106 is preferably adapted to harvest a viable tissue sample without tearing, crushing or otherwise damaging the tissue to maximize viability. A viable tissue sample can have one or more viable cells within it and can have a proportion of cells which can be capable of migrating from the tissue sample to a tissue scaffold, and/or used in tissue grafts other tissue engineering techniques. For example, in some embodiments, at least about 50 percent, and more preferably greater than 70 percent, of cells in a harvested tissue sample can represent living cells capable of migrating from the tissue sample. Virtually any type of tissue can be harvested with this device, including cartilage (and including in particular articular cartilage in a patient's knee), fibrocartilage, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood and combinations thereof. In one embodiment useful for cartilage repair, the tissue can include cartilage tissue, meniscal tissue, ligament tissue, tendon tissue, periosteal tissue, or synovial tissue. As will be described in more detail below, the tissue harvesting tip 106 can be driven by the drive mechanism 112 so as to harvest viable tissue samples which are substantially free of or have little bone tissue contamination.

Figure 17A:
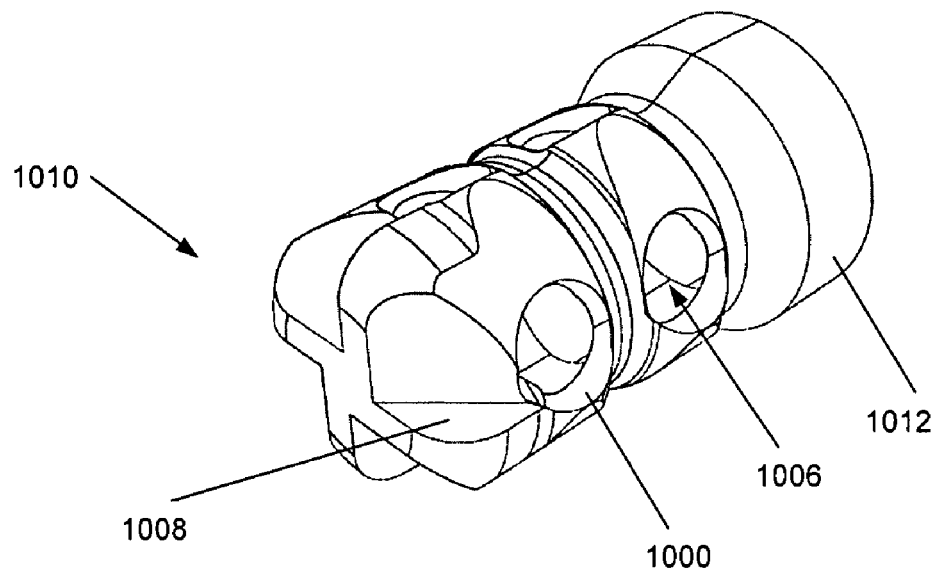
FIG. 17A is a distal perspective view of the tissue harvesting tip shown in FIG. 16.
Figure 17B:
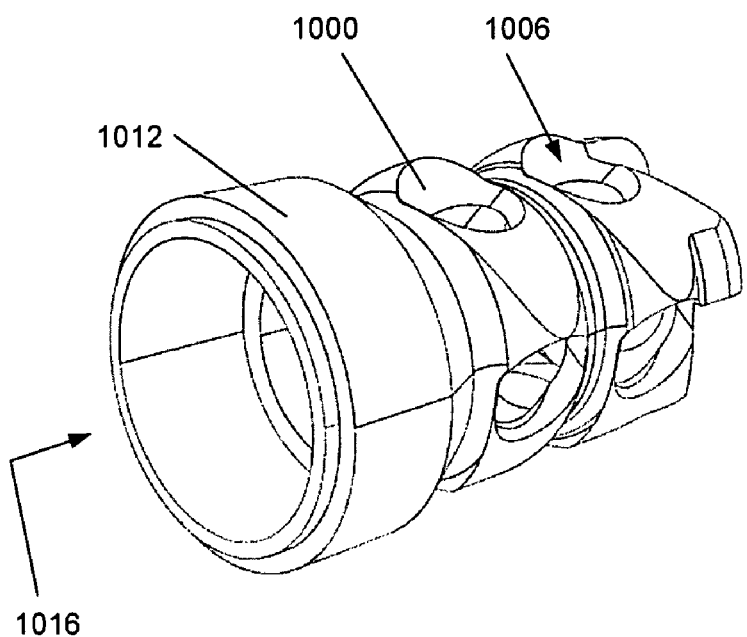
FIG. 17B is a proximal perspective view of the tissue harvesting tip shown in FIG. 16.
Figure 25:
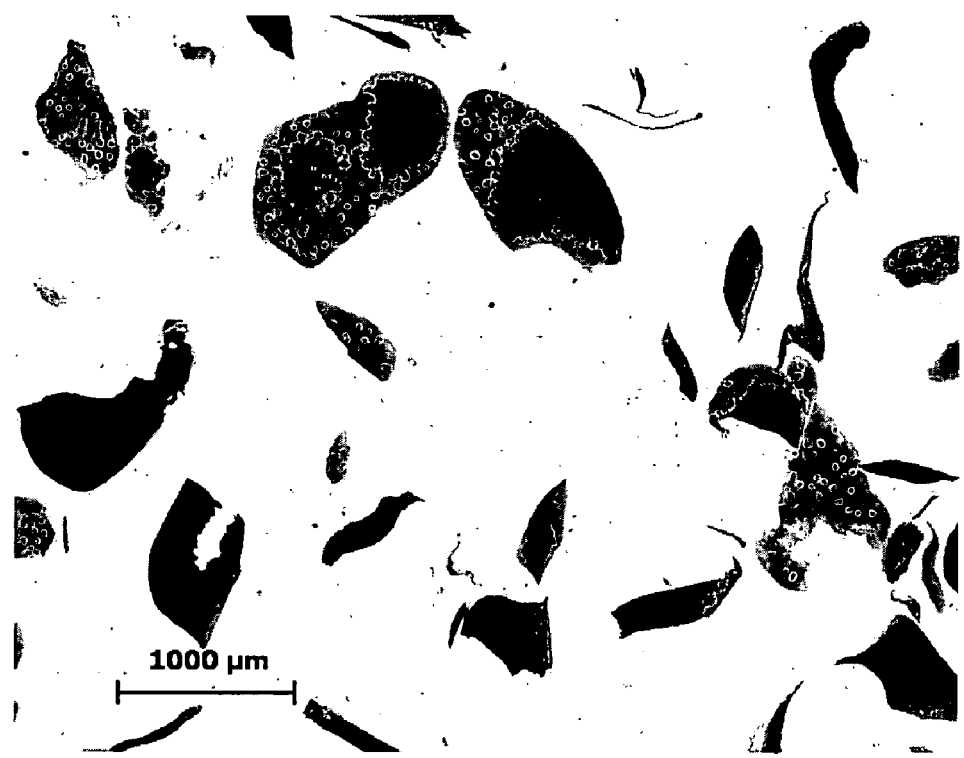

In one exemplary embodiment, shown in FIGS. 17A-B, the tissue harvesting tip 106 can be substantially cylindrical in shape and can be hollow or have a lumen formed therein. Several cutting elements can be disposed on the tissue cutting tip 106. While the cutting elements can have a variety of shapes, configurations and sizes, in one exemplary embodiment, the cutting elements can be effective to morselize tissue into particles having a size range of about 0.01 to 3 mm$^3$. However, the particles of tissue can be a variety of sizes. For example, in other embodiments, the morselized tissue particles can have a size in a range of less than 1 mm$^3$, in the range of about 0.5 to 1 mm$^3$, in the range of about 1 to 2 mm$^3$, or in the range of about 2 to 3 mm$^3$. In some embodiments, about 90 percent or more of the excised tissue particles in a tissue sample can fall within such a size ranges. In other embodiments, about 50 percent or more of the excised tissue particles in a tissue sample can fall within such a range of sizes. By way of illustration only, FIG. 25 shows actual tissue particles harvested with the tissue harvesting tip 106. In many cases, harvesting tissue particles of a specific size can have advantages. Tissue particles that are too small may have a greater proportion of cells on their periphery, which are more likely to die during the harvest, and as a result the viability of the tissue may be low. Tissue particles that are large may have fewer cells on the periphery, but on the other hand may have a large portion of cells which are encased in the extracellular matrix, and therefore can be slow to migrate out.

As shown in FIGS. 17A-B, the cutting elements can be cutting surfaces 1000 which can be disposed around the circumference of the tissue harvesting tip 106 so as to excise tissue upon its rotation. Openings 1006 can be formed in the wall of the tissue harvesting tip 106 to allow excised pieces of tissue to pass into the tip 106, where they can exit through port 1016 into the inner lumen 900 of the inner shaft 110. The size of the cutting surfaces 1000, as well as the size of openings 1006, can be adapted to excise tissue into appropriately sized pieces promote later growth and/or incorporation of those tissues on a scaffold (or can be adapted for other applications). For example, in one embodiment the openings 1006 can be in a range of about 1 mm to 3 mm across, and in other embodiments can more preferably be about 2 mm across. Although in this embodiment, the tissue is harvested through openings 1006, the tissue harvesting tip 106 can have one or more cutting surfaces 1008 on its distal end 1010, which can be advantageous by allowing distal pressure on the device 90 and the tissue harvesting tip 106 to cut or drill into tissue. In other embodiments, the distal end 1010 of the tissue harvesting tip 106 can be smooth and/or have no cutting surfaces on its distal end 1010. The base portion 1012 of the tissue harvesting tip 106 can be solid and can be coupled to the shaft 110.

In the embodiment illustrated in FIGS. 17A-B, the tissue harvesting tip 106 includes eight cutting surfaces 1000 and eight openings 1006, although a range of cutting surfaces and openings can be employed. In addition, while in FIGS. 17A-B the cutting surfaces 1000 are oriented such that they excise tissue upon rotation of the tissue harvesting tip 106, in other embodiments, the cutting surfaces 1000 can be disposed such that reciprocating motion of the tissue harvesting tip 106 can excise tissue. For example, the cutting surfaces 1000 can be oriented around the openings 1006 in more than one direction.

Figure 18A:
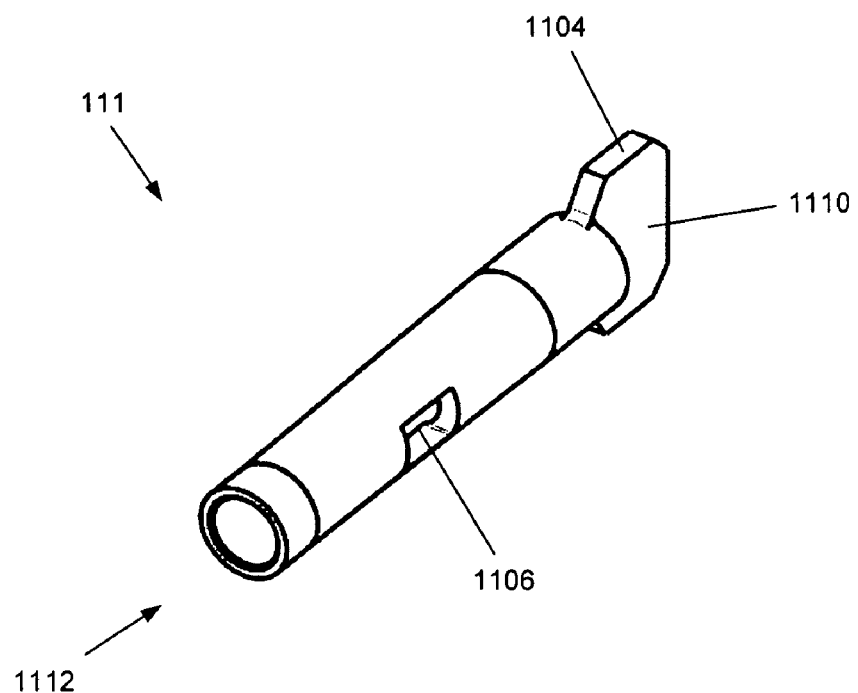
FIG. 18A is a distal perspective view of the drive coupling shown in FIG. 16.
Figure 18B:
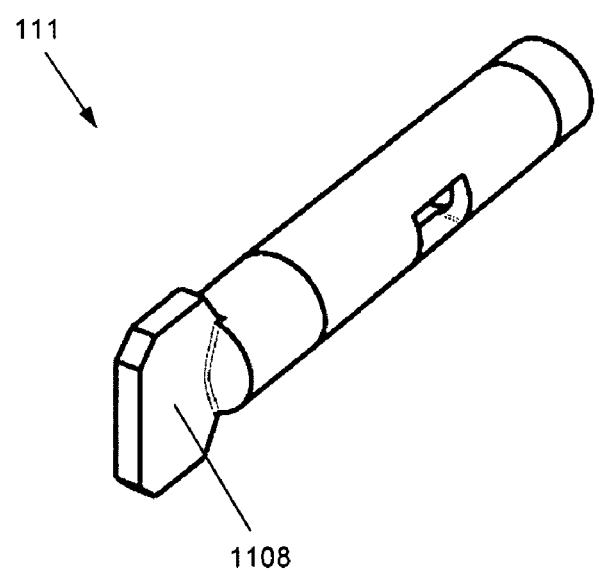
FIG. 18B is a proximal perspective view of the drive coupling shown in FIG. 16.

As shown in FIG. 16 and with further reference to FIGS. 18A and 18B, the inner shaft 110 can be mated to the drive coupling 111. While virtually any shape and size is possible, in the illustrated embodiment, the drive coupling 111 includes a cylindrical shaft portion 1102 adapted to be coupled to the inner shaft 110 such that lumen 900 is extended into lumen 1112. In this manner, shaft portion 1102 can provide an extension to the inner shaft 110 and lumen 900 such that the shaft portion 1102 and inner shaft 110 together comprise shaft 902 and the lumen 900 extends through the inner shaft 110 and the drive coupling 111. One or more openings or exit ports 1106 can be formed in a sidewall defining the lumen 900. As shown, the exit ports are formed in the shaft portion 1102. In other embodiments they can be formed in the inner shaft 110. The exit ports 1106 can be any shape and size, but are shown as rectangular openings on opposed sides of the drive coupling 111. In many embodiments, the exit ports 1106 can be sized such that tissue and/or fluid can be drawn therethrough during operation of the device 90, as will explained in more detail below. In some embodiments, the exit ports 1106 can be formed in the inner shaft 110 rather than the drive coupling 111. The drive coupling 111 can further include a tab 1104 disposed at its proximal end for engaging the drive mechanism 112. As shown the tab 1104 is formed by a blade-like element which provides two opposing surfaces 1108, 1110. A variety of other configurations of tabs 1104 are possible, including a variety of shapes and sizes, surface features, multiple-bladed elements (e.g., intersecting blades in the form of an "x" or otherwise). Furthermore, in other embodiments other kinds of elements can be used to couple the drive coupling 111 to the drive mechanism 112, including gears, drive shafts, and so on.

Returning to FIG. 13, exemplary fluid flow through the cutter subassembly 500 during operation of the device 90 can be represented by the arrows. In general, and by way of example only, in use the inner shaft 110 can rotate within the outer tube 102. Excised tissue and fluid can flow through the lumen 900 in the inner shaft 110. Excised tissue and/or fluid captured by the tissue harvesting tip 106 can travel from distal end 108 of the inner shaft 106 to its proximal end 118 and into the drive coupling 111, e.g., under a vacuum force. As each exit port 1106 in the drive coupling 111 aligns with the opening to the transfer tube 124, excised tissue and/or fluid can be drawn into the transfer tube 124 by a vacuum. FIG. 13, for example, shows the drive coupling 111 with two exit ports 1106, one exit port being aligned with the opening to the transfer tube 124. The nature of the flow into the transfer tube 124 can be changed by changing the size and shape of the exit ports 1106, as one skilled in the art will understand. In some embodiments, the drive coupling 111 and/or the mounting tube 126 can have an expanded interior space within area 602 that forms, for example, a cylindrical reservoir around exit ports 1106 such that as the inner shaft 110 rotates the exit ports 1106 are not blocked, but are often or always in communication with the transfer tube 124. Such an embodiment can be advantageous for reducing or eliminating any intermittent nature of the tissue and/or fluid flow through the transfer tube 124. As one skilled in the art will realize, the foregoing is by way of example only and a wide range of variations are possible.

Figure 19A:
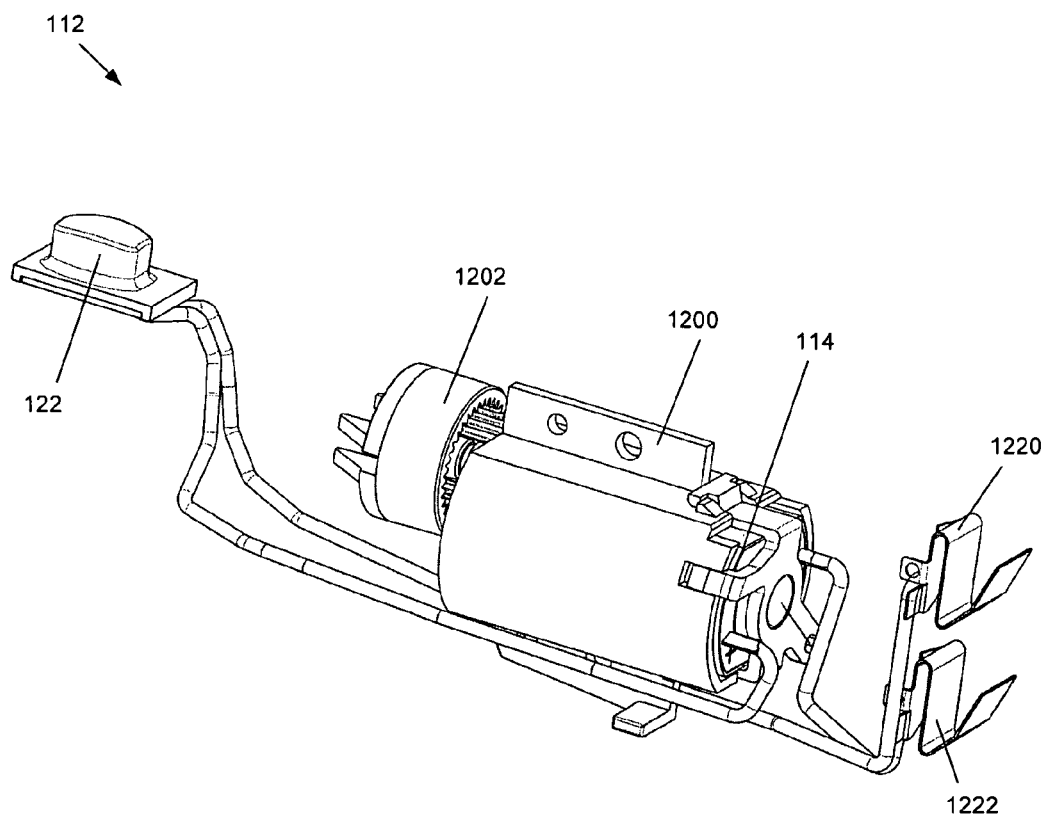
FIG. 19A is an assembly view of the drive mechanism shown in FIGS. 10-11B.
Figure 19B:
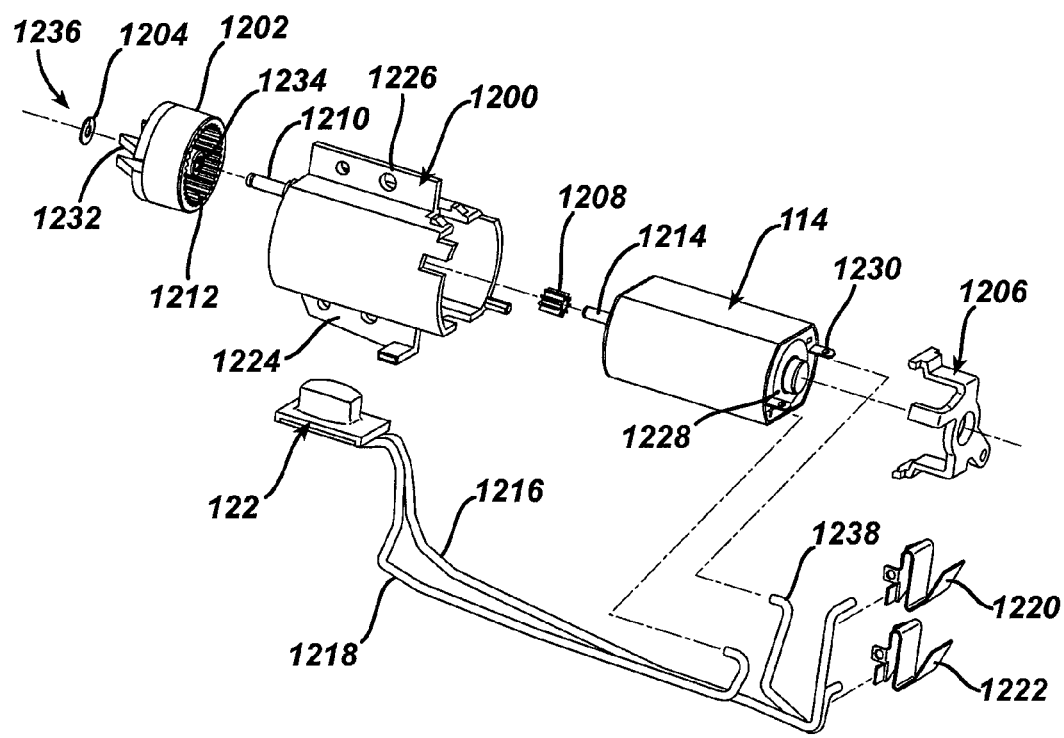
FIG. 19B is a exploded view of the drive mechanism shown in FIG. 19A.

The drive mechanism 112 also can have a variety of configurations. As shown in FIGS. 19A-19B, in one embodiment, the drive mechanism 112 converts electrical energy into mechanical energy, although it should be understood that a wide variety of drive mechanisms and power sources can be employed to impart a force (such as a rotational force or otherwise) to the tissue harvesting tip 106. In the illustrated embodiment, the drive mechanism 112 includes an electric motor 114 which can be virtually any AC or DC, synchronous or asynchronous, or other type of electric motor. The motor 114 can be disposed in a motor mount 1200, which can be shaped and size to hold the motor 114, e.g., as a sleeve. A retainer clip 1206 can be provided and can extend across the end of the motor 114 and can have tabs mating to the motor mount 1200 to secure the motor 114 within the motor mount 1200. The motor mount 1200 can have brackets 1224, 1226 extending from an external surface for mounting the motor mount 1200 to other objects, such as the interior of the handle housing 100. An alignment pin 1210 can extend proximally from the motor mount 1200. The drive mechanism 112 can also include an output gear 1202, which as shown can be in the form of a hollow cylinder with gear teeth 1212 formed on an interior surface thereof. The output gear 1202 can have an axle 1234 adapted to accept the alignment pin 1210 from the motor mount 1200. The mating of the alignment pin 1210 and the axle 1234 can orient the motor 114 such that a pinion gear 1208 attached to the drive spindle 1214 of the motor 114 can mesh with the gear teeth 1212 formed on the interior of the output gear 1202.

Figure 20:
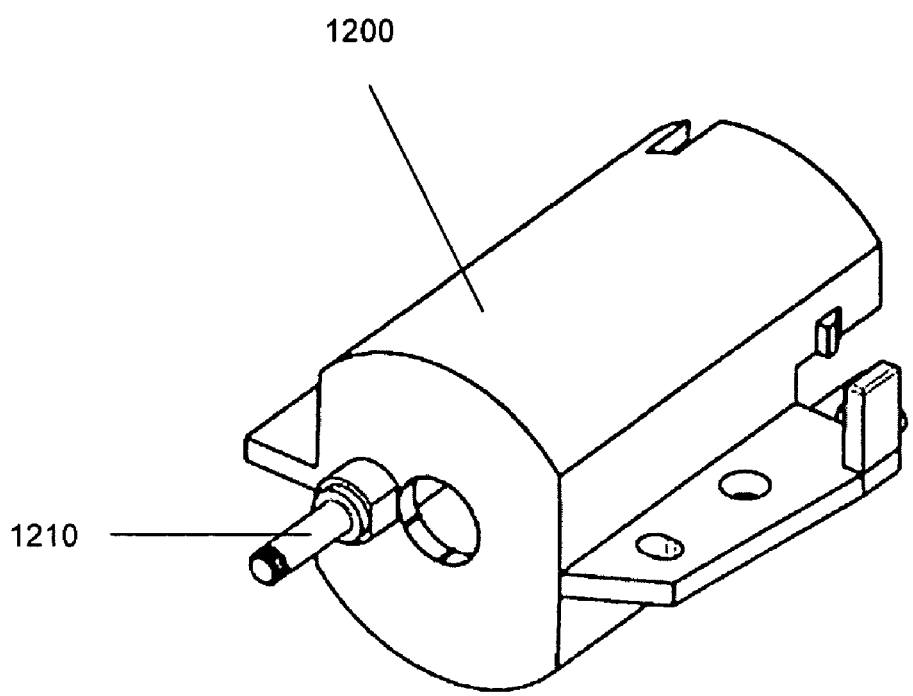
FIG. 20 is a perspective view of the motor mount shown in FIGS. 19A-19B.
Figure 21A:
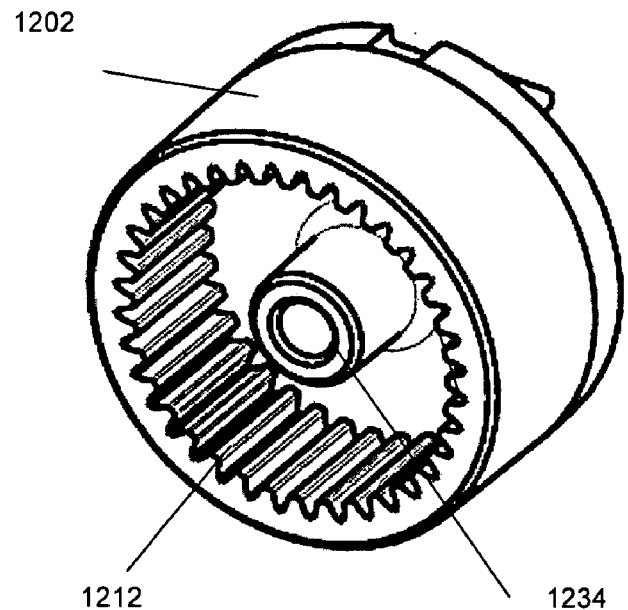
FIG. 21A is a proximal perspective view of the output gear shown in FIGS. 19A-19B.
Figure 21B:
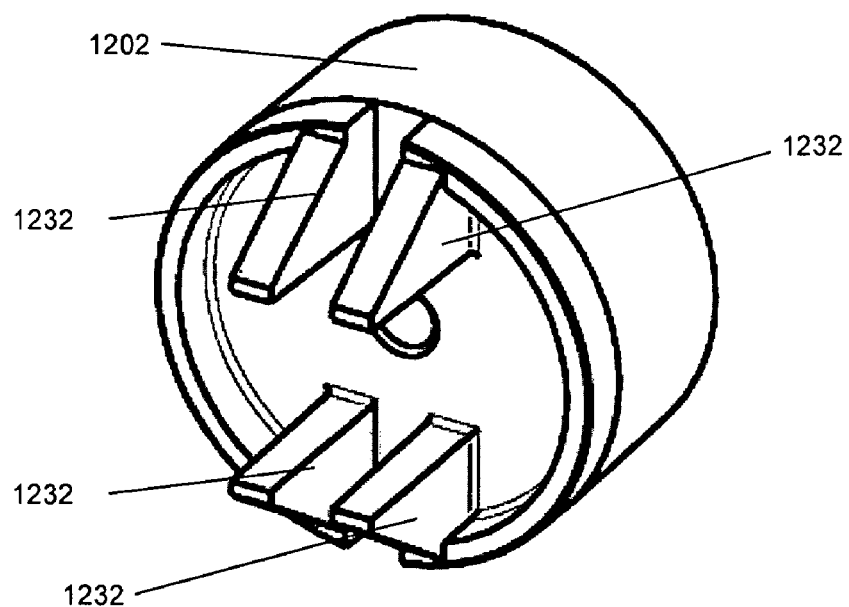
FIG. 21B is a distal perspective view of the output gear shown in FIGS. 19A-19B.

Any kind of rotational coupling between the motor and the tissue harvesting tip 106 or other cutting element can be used. In various embodiments, different size, type, and/or number of gears can be provided. In addition, the motor 114 and gears 1208 and 1212 can be selected to rotate the tissue harvesting tip 106 at about 100 rpm to 5000 rpm, and more preferably about 2000 to 3000 rpm. In some embodiments, the gear ratios and torque can be adapted to drive the tissue harvesting tip 106 when applied to soft tissue but not when applied to bone. For example, drive mechanism can be adapted to rotate the tissue harvesting tip such that the tissue harvesting tip 106 stops sufficiently fast upon contacting bone tissue (for example, subchondral bone, if the tissue being harvested is cartilage over bone) so as to produce a tissue sample having less than about 10% bone tissue contamination, or more preferably less than about 5% bone tissue contamination, or more preferably less than about 1% bone tissue contamination. As mentioned above, the tissue sample can be a viable tissue sample comprised of any of a wide range of tissue types. Such an effect can be produced by applying to the tissue harvesting tip 106 a torque of about 1 to 5 N-cm and more preferably about 3 to 4 N-cm. The motor and gear ratios can be adjusted to achieve the appropriate torque. For example, to achieve a torque of 4 N-cm, the motor can provide a torque of about 1 N-cm and can be coupled to a gearing mechanism with a gear ratio of about 4 to 1. The proximal face 1236 of the output gear 1202 can include a plurality of triangular finger tabs 1232 which extend away from the surface. As shown, the finger tabs 1232 can be arranged in two pairs to receive the tab 1104 of the drive coupling 111. In use, the torque provided by the motor 114 can rotate the pinion gear 1208, the output gear 1202 and the finger tabs 1232, which can apply a rotational force to the tab 1104 of the drive coupling and the inner shaft 110. The drive mechanism 112 can also include a retaining washer 1204 which can attach to the motor spindle 1210, securing the output gear 1202 against the pinion gear 1208 and the motor mount 1202. FIGS. 20 and 21A, 21B illustrate in more detail the motor mount 1200 and the output gear 1202, respectively, described above.

The drive mechanism 112 can further include a switch 122 for controlling the flow of electricity to the motor 114. As shown, the switch 122 is a single-pole push-to-actuate type, such that depression of the switch 122 completes a circuit and release of pressure on the switch 122 opens the circuit. However, virtually any type of switch, including rocker switches, sliding switches, on/off buttons, single-pole, double-pole, etc., are possible. The switch 122 can be connected to wires 1216, 1218. Wire 1216 can lead to the positive power terminal 1220, at which the positive end of a power source, such as the battery pack 120, can be connected. Wire 1218 can lead to the positive terminal 1218 of the motor 114. Wire 1238 can also be provided to connect the negative power terminal 1222 with the negative terminal 1230 of the motor 114. As shown, the switch 122 provides an open-positive circuit, that is, when the switch is open, the positive terminal 1228 of the motor 114 is open-circuited, while the negative terminal 1230 of the motor 114 is always connected to the negative power terminal 1222, which is connected to the negative end of the battery pack 120. However, virtually any switched circuit configuration, such as an open-negative circuit, is possible.

In some embodiments, the drive mechanism can rotate the inner shaft 110 and the tissue harvesting tip 106 in one direction, however in other embodiments the rotation of the shaft 110 can be reciprocating or the direction of rotation can be user-selectable, for example, with use of an AC power source, or a switch assembly providing alternate polarity to the motor 114. For reversing the direction, the polarity can be changed. Reciprocation can be achieved with appropriate motors and electronics. In such embodiments, the tissue harvesting tip 106 can be have cutting surfaces that are effective in either direction.

Figure 22:
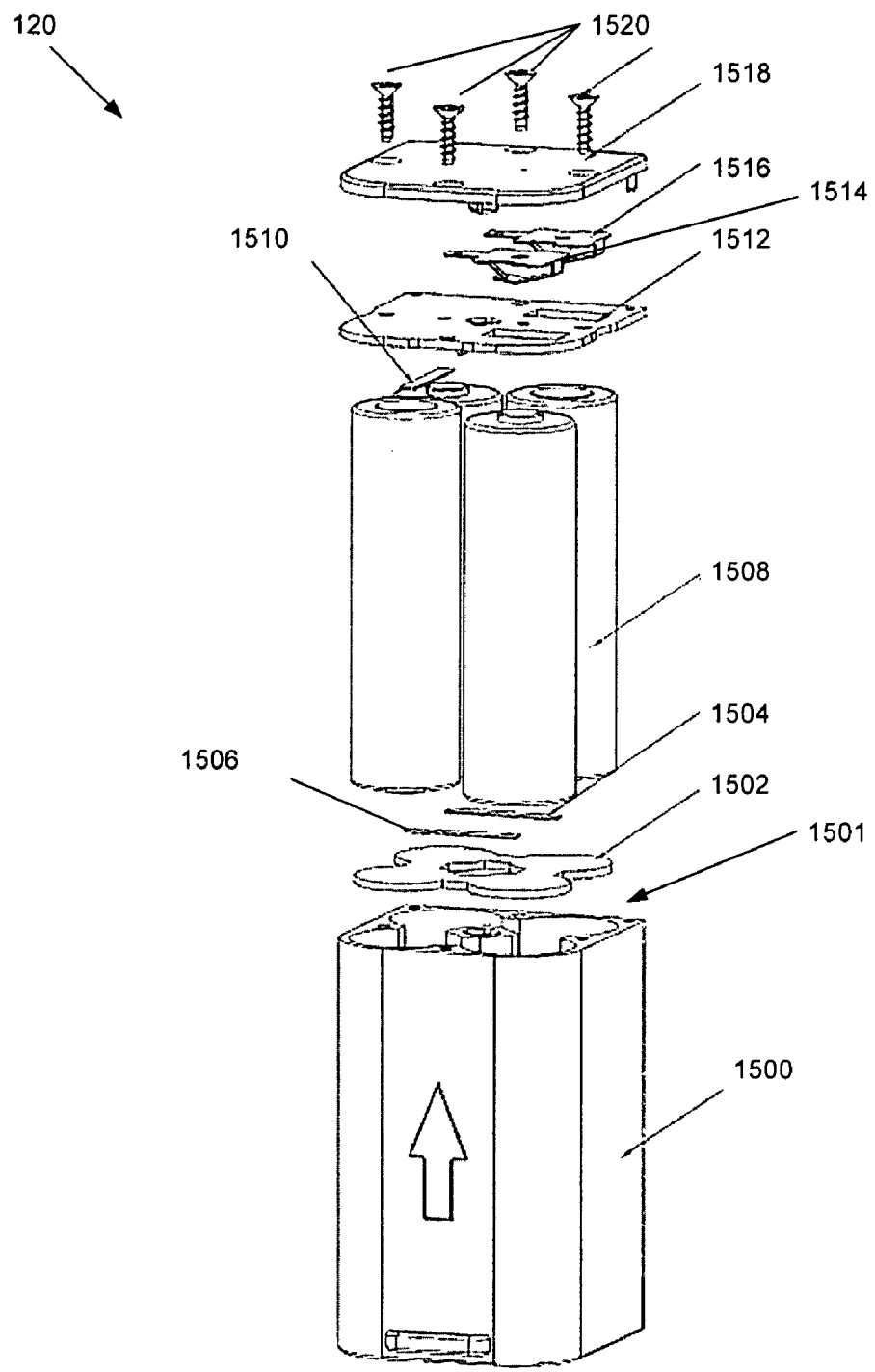
FIG. 22 is an exploded view of the battery pack shown in FIGS. 10-11B.

The battery pack 120, or other power source, can have a variety of configurations, but as shown in FIG. 22 it includes a case 1500 that is substantially rectangular and includes four receiving slots 1501 formed therein. The case can have a variety of shapes and sizes in order to accommodate various power sources, but in this embodiment, four AA size batteries 1508 are employed. A spacer 1502 can be disposed in the bottom of the case 1500. The spacer 1502 can be made of silicone, for example. The battery pack can also include shorting bars 1504, 1506, which can be rectangular bars formed of an electrically conductive material, in order to provide an electrical connection between adjacent terminals of the batteries 1508. Another shorting bar 1510 can be provided on the top surface of the batteries 1508, the shorting bars collectively arranged such that one electrical path is defined through the four batteries 1508. The battery pack 120 can further include a top seal 1512, which can also be made of silicone or another material such as rubber, plastic, and so on. Power source terminals 1514, 1516 can be provided as well. As shown, terminal 1514 is a positive terminal and terminal 1516 is a negative terminal, and these terminals 1514, 1516 can connected to power terminals 1220, 1222 shown in FIG. 19B, respectively. In other embodiments, terminal 1514 and 1220 can be the same terminal, and terminal 1516 and 1222 can be the same terminal. A cover 1518 can be disposed over the terminals 1514, 1516 and can be secured into place with screws 1520, bolts, adhesives, interference fits, interlocking tabs, rails, or other parts, or any of a wide variety of other means.

As previously mentioned, the tissue extraction and collection device 90 can also include a tissue collection device 128, which, as shown in FIG. 10, can be coupled to the transfer tube 124 via an inlet fitting 132. The tissue collection device can have a wide variety of configurations, but in the illustrated embodiment of FIGS. 23A-23B, it includes a container 130 defining a passageway therethrough from an inlet 1612 to an outlet 1622. As shown, the container 130 is a cylindrical tube that is substantially transparent, however, shafts, housings, coverings, cylinders of virtually any shape and size can be used. As one skilled in the art will understand, the container 130 can be virtually any shape and size suitable to pass tissue and/or fluid therethrough. For example, it can have a cross-sectional shape in the form of a rectangle, square, oval, etc., and can have a channel formed therein of the same or different shape. The inlet fitting 132 can have a first exterior portion 1600 that is adapted to couple directly to the transfer tube 124, for example the diameter of the first portion 1600 can be such that the transfer tube 124 can slide or be placed over it. However, in other embodiments, the first portion 1600 can be mated to a complementary fitting on the transfer tube 124 so as to provide a fluid tight seal when the tissue collection device 128 is inserted into the handle housing 100 of the device 90 and when the connection mechanism 136 is engaged. In other embodiments, additional fittings, seals, latches, adhesive, or any of a range of coupling elements can be employed. A second portion 1602 can be adapted to coupled to the container 130. The outlet fitting 134 can also have first and second portions, and the first portion 1606 can be adapted to couple to a vacuum source, e.g., via a tube, fitting, shaft, and so on. The second portion 1604 can be adapted to couple to the container 130. The outlet fitting 134 can be removably coupled to the container 130, e.g., via tabs engaged by rotating the outlet fitting 134 or other means, to allow access to the components within the container 130. The container 130, inlet fitting 132, and outlet fitting 134 can define a passageway 1612 through which, during operation of the device 90, excised tissue and/or fluid can flow (e.g., under the force of the vacuum source coupled to the outlet fitting).

Figure 23A:
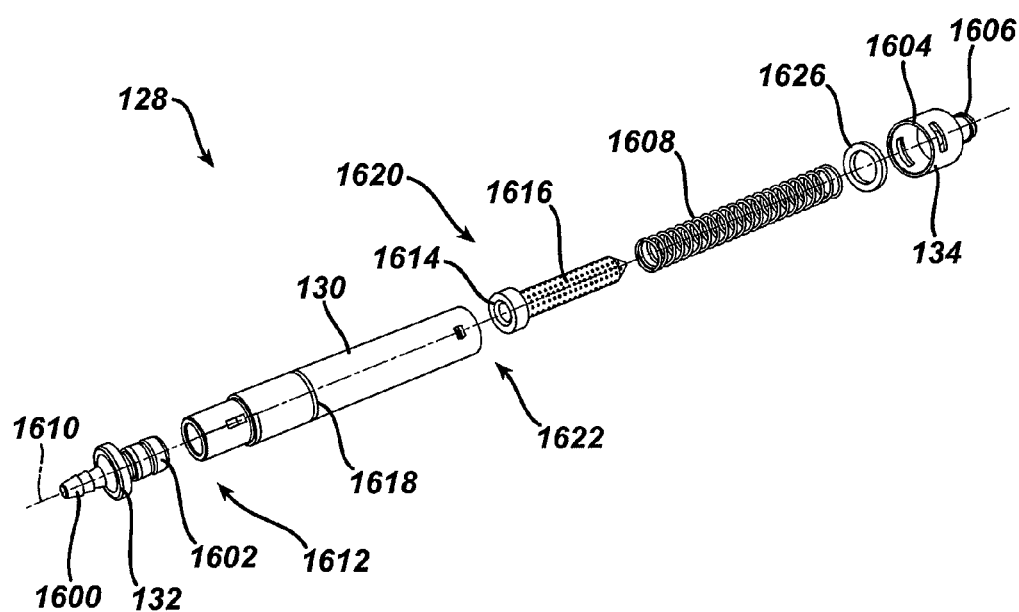
FIG. 23A is an exploded view of the tissue collection device shown in FIGS. 8A-11B.
Figure 23B:
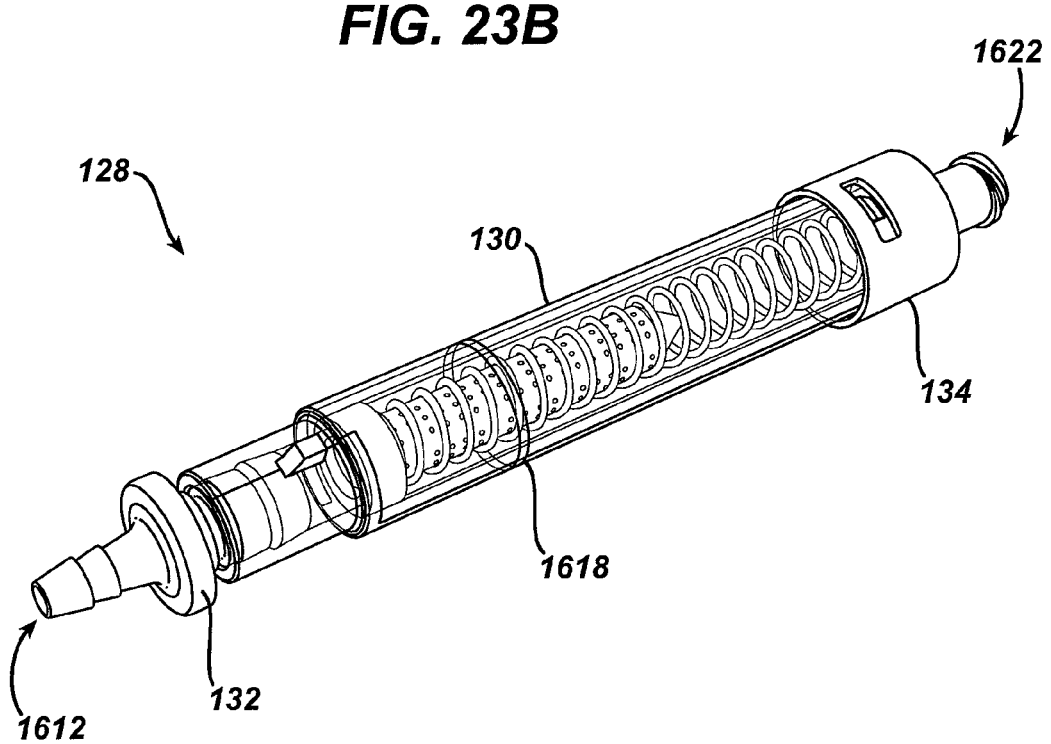
FIG. 23B is an assembly view of the tissue collection device shown in FIG. 23A.

As shown in FIGS. 23A and 23B, the tissue collection device 128 can further include a tissue collection chamber 1620, which in an exemplary embodiment is substantially cylindrical with a flanged area 1614 and a straining element 1616. The tissue collection chamber 1620 can be shaped and sized to fit within the container 130 such that substantially all tissue and/or fluid flowing therethrough flows through the tissue collection chamber, and can also be adapted for movement within the container 130. For example, the flanged portion 1614 can be nearly the same diameter as the interior opening of the container 130, allowing little or no tissue/fluid to pass between the tissue collection device 1620 and the sidewalls of the container 130 yet still allow for translation of the tissue collection chamber 1620 within the container 130, e.g., along a longitudinal axis such as axis 1610. In other embodiments, the flanged portion 1614 can be narrower and allow some tissue and/or fluid to pass through to the outlet 1622 without going through the tissue collection chamber 1620. The straining element 1616 can have a mesh, perforations, filter, screen or other element formed therein or thereon for allowing fluid to pass while retaining or capturing pieces of tissue (e.g., excised tissue). The size of the openings in the mesh, perforations, and so on, can be chosen to capture pieces of tissue suitable for later use (e.g., on a tissue scaffold) while passing others, although in many embodiments, the size can be such that there is a minimal loss of tissue therethrough. For example, in one embodiment, the mesh can have openings about 0.5 mm wide. Although shown as cylindrical in shape, the straining element 1616 can have a wide variety of shapes and sizes. For example, the straining element 1616 can include a perforated or mesh disk disposed at the bottom of the flanged portion 1614, or can include multiple cylinders each extending from the flanged portion 1614, and so on. In use, the flow of fluid can carry pieces of tissue into the straining element 1616 of the tissue collection chamber 1620, and gradually blocking or impeding fluid flow through the straining element 1616 (e.g., the perforations or mesh, etc.). As tissue continues to be collected and fluid continues to be drawn towards the outlet 1622 by the vacuum source, the tissue collection chamber 1620 can translate within the container 130 (in the illustrated embodiment, such translation can occur along the axis 1610 towards the outlet 1622 and/or outlet fitting 134). The degree of translation or displacement of the tissue collection chamber 1620 can be correlated to indicate the amount of collected tissue therein, as will be discussed below.

In some embodiments, the tissue collection device 128 can further include a biasing element 1608 arranged to bias the translation of the tissue collection chamber 1620 along (or at least partially along) an axis, such as axis 1610. The biasing element 1608 can have a variety of forms, but as shown in the illustrated embodiment, the biasing element 1608 is in the form of a coil spring which on one end abuts the tissue collection chamber 1620 and on the opposing end abuts the outlet fitting 134. An O-ring 1626 or washer can be disposed at the interface between the container 130 and the outlet fitting 134. The straining element 1616 can be received through the biasing element 1608, such that as the straining element 1616 fills, the spring is gradually compressed. The biasing element 1608 can thus oppose the suction or vacuum force on the tissue collection chamber 1620. As previously mentioned the displacement of the tissue collection chamber 1620 within the container 130 along the axis 1610 can be correlated to indicate the amount of tissue within the tissue collection chamber 1620. Other types of springs can be used, as well as elastomeric materials (e.g., a flexible spacer or band) to form the biasing element 1608.

A visual indicator, such as visual reference indicator 1618, can be inscribed on the container 130 for indicating the displacement of the tissue collection chamber 1620 within the container 130. In the illustrated embodiment, the visual indicator is a reference line, however a wide range of visual indicators are possible. For example, in other embodiments, multiple lines can be provided, each line corresponding to an amount of tissue collected in the tissue collection chamber 1620 and/or indicating that the amount of collected tissue is appropriate for a particular procedure. In addition, thick bars indicating a range can be provided. Visual indicators with color patterns to convey information can also be provided. A corresponding visual indicator such as a line can be inscribed on the flanged portion 1614 of the tissue collection chamber 1620 so that in use, when a desired amount of tissue has been collected, the line on the container 130 overlays the line on the tissue collection chamber 1620. In use, the visual reference indicator 1618 or other visual indicator can be viewed through a sighting port 138 formed in the container 130.

While shown as transparent, the container 130 can be opaque and/or translucent as well. For example, the container 130 can be partially formed of a transparent or translucent material, which can be viewed through the sighting port on the container 130. In other embodiments, the container 130 can be opaque and a visual indicator can extend outside of the container 130, for example, the visual indicator can be a protruding tab that is coupled to the tissue collection chamber 1620.

Alternatively, the translation or other movement of the tissue collection chamber 1620 can activate a feedback mechanism to indicate the amount of collected tissue or end tissue collection when the desired amount of tissue has been collected. In one exemplary embodiment, the feedback mechanism is a switch. The switch, for example, can include a push-type switch or button within the container 130 and disposed on the inlet fitting 132, outlet fitting 134 or within the container 130 so as to be contacted, released or otherwise actuated by the movement of the tissue collection chamber 1620. The switch can activate an indicator light or an audible indicator or alarm, or can alert a computer or electronic system to the status of the tissue collection chamber 1620. Actuation of a switch could also stop the vacuum source and/or cut power to the drive mechanism 112.

It should also be understood that the tissue collection chamber 1620 can be adapted to exhibit movement other than translation. For example, in some embodiments the container 130 and the tissue collection chamber 1620 can have screw threads formed thereon (on the interior of the container 130 and on flanged area 1614, for example) which can cause the tissue collection chamber 1620 to rotate as it fills with tissue. This rotation (which can coincide with translation as well) can actuate a switch or be used in conjunction with a visual reference indicator on the container 130. In such an embodiment, the visual reference indicator can be reference line marked longitudinally on the container 130 for determining the appropriate amount of tissue collected.

Figure 24A:
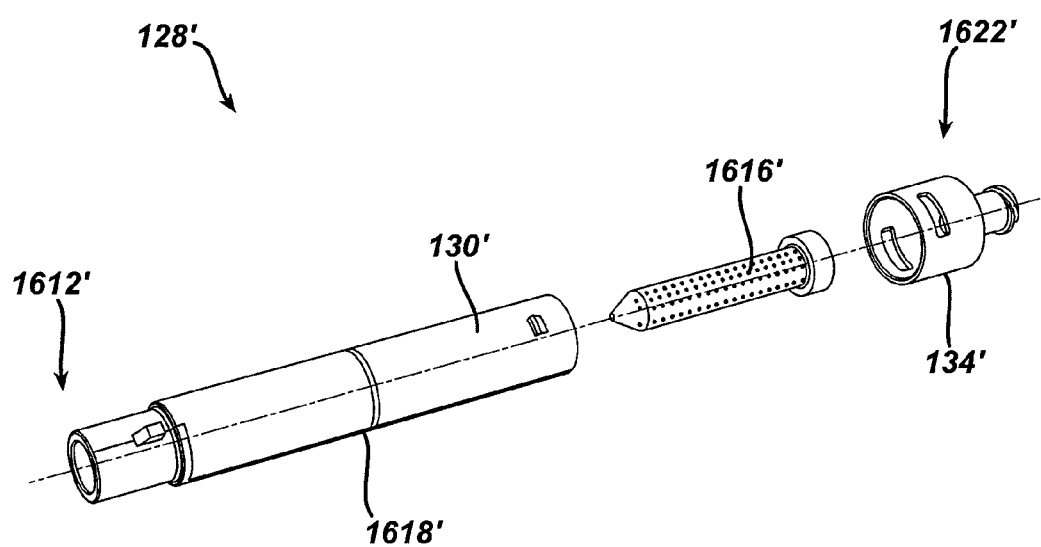
FIG. 24A is an exploded view of an alternate embodiment of a tissue collection device.
Figure 24B:
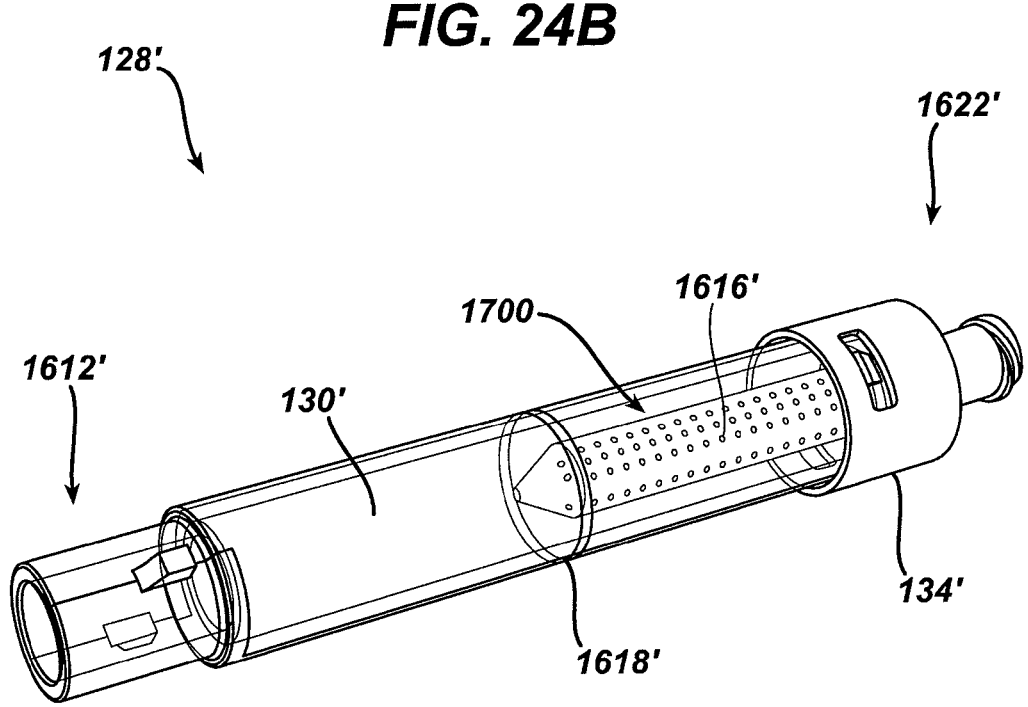
FIG. 24B is an assembly view of the tissue collection device shown in FIG. 24A; and, FIG. 25 is a photograph of an exemplary sample of viable tissues harvested using the methods and devices described herein.

Another exemplary embodiment of a tissue collection device 128' is shown in FIGS. 24A-B and can involve no translation or other movement of a tissue collection chamber or other element. As shown, the tissue collection device 128' can include a container 130' with a visual reference indicator 1618' disposed thereon. The tissue collection device 128' also can be configured such that a straining element 1616' is disposed against or attached to the outlet fitting 134'. The straining element 1616' can have a mesh, perforations, filter, screen or other element formed therein or thereon for allowing fluid to pass while retaining or capturing pieces of tissue (e.g., excised tissue). In use, under the influence of a vacuum fluid can enter the inlet 1612' (which in some embodiments can have an inlet fitting 132' coupled thereto, although not shown in FIGS. 24A-B) and flow towards the outlet 1622', passing through the straining element 1616'. Tissue particles of a desired size, which can be suspended in the fluid, can be captured by the straining element 1616' and accumulate in the space 1700 between the container 130' and the straining element 1616'. The reference indicator 1618' can be used to determine that a desired amount of tissue has been collected. The device 128' can be configured for various amounts of tissue as well as the size of particles. In use, as tissue accumulates, the level of collected tissue can build towards and reach the indicator 1618', and for example can be visually observed. Collected tissue can be removed by pumping fluid from the outlet 1622' to the inlet 1612' so as to remove tissue through the inlet 1612'.

As one skilled in the art will understand, the tissue collection device can be adapted or sized to collect virtually any amount of tissue and/or to indicate when virtually any amount of tissue has been collected through any of the foregoing configurations. By way of example only, in one embodiment, the tissue collection device 128 can be adapted to collect and/or indicate a mass of tissue harvested in a range of about 50 to 1000 mg, and more preferably about 200 to 400 mg.

In use, a tissue collection device 128 can be inserted into the handle housing 100 and locked into position with the connection mechanism 136. The device 90 can be connected to a vacuum source (preferably at the outlet fitting 134 of the tissue collection device 128) that is effective to create a vacuum within the lumen 900 of the inner shaft 110. Batteries can be loaded into the battery pack 120 and the cover 140 can be put into place on the handle housing 100, enclosing the battery pack 120 therein. In other embodiments, the device 90 can be connected to other electric power sources. The tissue harvesting tip 106 can be positioned near a source of appropriate tissue, for example, cartilage in the body.

Actuation of switch 122 can cause power from the battery pack 120 to be delivered to the motor 114, which can provide a rotational force to the inner shaft 110 via gears 1208, 1202 and drive coupling 111. Upon rotation of the inner shaft 110 and the tissue harvesting tip 106, the tip 106 can be effective to excise pieces of tissue from the selected tissue site. This tissue, along with any fluid present at the tissue harvesting site (be it naturally occurring and/or surgically introduced fluid) can be transported via the vacuum force through the tissue harvesting tip 106 and into the lumen 900 of the inner shaft 110. Excised tissue and fluid can be transported down the lumen 900 to one or more exit ports 1106 formed in the wall of drive coupling 111. As each exit port 1106 aligns with an opening to transfer tube 124 (that is, as the inner shaft 110 and drive coupling 111 rotates), the suction of the vacuum force can draw the tissue and fluid therethrough, resulting in an intermittent flow into the transfer tube 124. The tissue and fluid can be transported through transfer tube 124, past inlet fitting 132 and into the tissue collection device 128. Tissue pieces can be collected in the tissue collection chamber 1616, gradually blocking or impeding fluid flow therethrough. The suction can cause the tissue collection chamber 1620 to move (for example, to translate) within the container 130 of the tissue collection device, and such movement can be correlated to the amount of collected tissue, e.g., with a visual or other indicator, for example by viewing the position of the tissue collection chamber 1616 through sighting port 138 formed in the handle housing 100. As previously mentioned, in some exemplary embodiments, for example, about 50 to 1000 mg, and more preferably about 200 to 400 mg, can be harvested, although any amount is possible. The switch 122 can be released, cutting power to the motor 114 and ending the harvesting of tissue.

The vacuum source can be deactivated and detached from outlet fitting 134, and the tissue collection device 128 can be moved out of the handle housing, and outlet fitting 134 (or in some cases inlet fitting 132) can be detached so that the tissue collection chamber 1620 can be accessed and/or removed. In other embodiments, the tissue collection device 128 can be removed from the handle housing 100. The collected tissue can be emptied onto a tissue scaffold or matrix suitable for creating/growing a tissue implant. In some embodiments, the tissue can be removed from the tissue collection device 128 by manually removing it from the tissue collection chamber, however in other embodiments, a flow of fluid can be directed through the tissue collection device 128 from the outlet 1622 to the inlet 1612 (for example, a fluid flow that is the reverse of the flow that collected the tissue during harvesting), which can cause the collected tissue and fluid to flow out of inlet fitting 132. In some embodiments, saline can be injected through the outlet fitting 134, dislodging the tissue in the tissue collection chamber 1620 and ejecting it through the inlet fitting 132. The collected tissue can also be placed into a tissue dispersion device for dispersing the tissue on a tissue scaffold or for other processing of the tissue (such as mincing the tissue, etc.). The collected tissue can be implanted at a desired surgical site within the tissue scaffold, in many cases repairing a defect in the patient's soft tissue and/or bone, and promoting healing at the site.

Further information on devices and methods for extracting tissue can be obtained with reference to U.S. Patent Publication No. 2004/0193071, the teachings of which are hereby incorporated by reference in their entireties.

The devices disclosed herein can be designed to be disposed of after a single use, or they can be designed to be used multiple times. In either case, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

One skilled in the art will appreciate further features and advantages based on the above-described embodiments. Accordingly, the application is not to be limited by what has been particularly shown and described, except as indicated by the appended claims. All publications and references cited herein are expressly incorporated herein by reference in their entirety.

What is claimed is:

1. A tissue extraction and collection device, comprising:
    an outer tube;
    a shaft rotatably disposed within the outer tube and having a tissue harvesting tip disposed at a distal end thereof, the tissue harvesting tip being effective to excise tissue upon rotation thereof; and
    a tissue collection device coupled to the outer tube for receiving excised tissue and fluid flow therefrom, the tissue collection device being configured to indicate an amount of excised tissue collected therein via one or more indicators included in the tissue collection device, the one or more indicators being effective to indicate displacement of at least a portion of the tissue collection device, the displacement resulting from collection of tissue in the tissue collecting device which overcomes a spring bias.

2. The device of claim 1, wherein the tissue collection device comprises:
   a substantially transparent portion and a tissue collection chamber disposed therein so as to be at least partially viewable through the substantially transparent portion; and,
   one or more visual indicators disposed on any of the substantially transparent portion or the tissue collection chamber to indicate a displacement of the tissue collection chamber which corresponds to the amount of tissue in the tissue collection chamber.

3. The tissue collection device of claim 2, wherein the visual indicator is adapted to indicate when about 50-1000 mg of tissue is disposed in the tissue collection chamber.

4. The device of claim 1, wherein the tissue collection device comprises a container having an inlet and outlet for receiving fluid flow therethrough and a tissue collection chamber disposed within the container.

5. The device of claim 4, wherein the tissue collection chamber is translatable along a longitudinal axis thereof such that fluid flow through the container is effective to translate the tissue collection chamber within the container, the indicator indicating longitudinal displacement of the tissue collection chamber within the container.

6. The device of claim 5, further comprising a biasing element biasing the tissue collection chamber along the longitudinal axis thereof, wherein fluid flow through the container is effective to overcome the biasing element to translate the tissue collection chamber within the container such that the displacement of the tissue collection chamber corresponds to an amount of tissue in the tissue collection chamber.

7. The device of claim 4, wherein the tissue collection chamber includes a straining element for collecting tissue and passing fluid.

8. The device of claim 7, wherein the straining element comprises any of a mesh, a filter, a screen, and a perforated surface.

9. The device of claim 4, wherein at least a portion of the tissue collection chamber extends across a lumen formed in the container such that substantially all fluid flow through the container flows through the tissue collection chamber.

10. The device of claim 1, wherein the tissue collection device includes a substantially transparent portion and a tissue collection chamber disposed therein so as to be at least partially viewable through the substantially transparent portion, and wherein the indicator comprises one or more visual indicators disposed on any of the substantially transparent portion or the tissue collection chamber to indicate the amount of tissue in the tissue collection device.

11. The tissue collection device of claim 10, wherein the visual indicator is adapted to indicate when about 50-1000 mg of tissue is disposed in the tissue collection device.

12. The device of claim 1, further comprising a handle housing from which the outer tube extends.

13. The device of claim 1, further comprising a driver mechanism coupled to the shaft for rotating the tissue harvesting tip.

14. The device of claim 1, further comprising a port for coupling to a vacuum source, the vacuum source being effective to draw tissue through at least a portion of the tissue collection device.

15. A tissue extraction and collection device, comprising:
   an outer tube;
   a shaft rotatably disposed within the outer tube and having a tissue harvesting tip disposed at a distal end thereof, the tissue harvesting tip being effective to excise tissue upon rotation thereof; and
   a tissue collection device coupled to the outer tube for receiving excised tissue and fluid flow therefrom, the tissue collection device having
   a container having an inlet and outlet for receiving fluid flow therethrough,
   a tissue collection chamber movably disposed within the container, wherein the tissue collection chamber moves in response to an amount of tissue collected in the chamber against a bias of a spring, and
   an indicator effective to indicate longitudinal displacement of the tissue collection chamber within the container.

16. The device of claim 15, wherein the tissue collection device is coupled to the outer tube by a transfer tube extending through a housing coupled to a proximal end of the outer tube.

17. The device of claim 15, wherein the container comprises a substantially transparent cylindrical tube.

18. The device of claim 15, wherein the tissue collection chamber includes a straining element configured to allow fluid to pass therethrough while preventing passage of excised tissue.

19. The device of claim 15, wherein the tissue collection device further includes a biasing element configured to bias the tissue collection chamber along a longitudinal axis of the container.

20. The device of claim 15, wherein the indicator comprises a reference line on the container.

21. A tissue extraction and collection device, comprising:
   a housing configured to be grasped by a user;
   an outer shaft extending distally from a distal end of the housing;
   an inner shaft rotatably disposed within the outer shaft and having a tissue harvesting tip disposed at a distal end thereof, the tissue harvesting tip being effective to excise tissue upon rotation thereof;
   a container removably coupled to the housing and in fluid communication with the outer shaft; and
   a tissue collection chamber movably disposed within the container and biased via a spring toward one of a proximal end and a distal end of the container, the tissue collection chamber being configured to receive and retain tissue excised by the inner shaft while allowing fluid to flow therethrough.

22. The device of claim 21, further comprising an indicator on one of the container and the tissue collection chamber for indicating an amount of tissue retained within the tissue collection chamber.

23. The device of claim 21, further comprising an indicator on one of the container and the tissue collection chamber for indicating longitudinal displacement of the tissue collection chamber within the container.

24. The device of claim 21, wherein movement of the tissue collection chamber corresponds to an amount of tissue collected in the chamber.

25. A tissue extraction and collection device, comprising:
   an outer tube;
   a shaft rotatably disposed within the outer tube and having a tissue harvesting tip disposed at a distal end thereof, the tissue harvesting tip being effective to excise tissue upon rotation thereof; and
   a tissue collection device coupled to the outer tube for receiving excised tissue and fluid flow therefrom, a portion of the tissue collection device being spring biased and configured to translate along a longitudinal axis of the tissue collection device as tissue is collected therein.

26. The device of claim 25, wherein the tissue collection device includes an indicator effective to indicate an amount of tissue collected therein.

27. The device of claim 25, wherein translation of the portion of the tissue collection device corresponds to an amount of tissue collected in the tissue collection device.

* * * * *